United States Patent
Evangelista et al.

(10) Patent No.: US 12,409,178 B2
(45) Date of Patent: *Sep. 9, 2025

(54) METHODS AND COMPOSITIONS COMPRISING A KRas$^{G12C}$ INHIBITOR AND A VEGF INHIBITOR FOR TREATING SOLID TUMORS

(71) Applicant: Genentech, Inc., South San Francisco, CA (US)

(72) Inventors: Marie Evangelista, San Francisco, CA (US); Mark Andrew Merchant, Redwood City, CA (US); Jennifer Lee Schutzman, Belmont, CA (US); Ting-Kun Mark Lin, Mill Valley, CA (US); Stephanie Royer Joo, San Diego, CA (US); Sandhya Vinayak Mandlekar, Foster City, CA (US); Stuart G. Lutzker, Walnut Creek, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/663,549

(22) Filed: May 14, 2024

(65) Prior Publication Data

US 2024/0299392 A1     Sep. 12, 2024

Related U.S. Application Data

(63) Continuation of application No. 17/524,050, filed on Nov. 11, 2021, now Pat. No. 12,016,862.

(60) Provisional application No. 63/113,609, filed on Nov. 13, 2020.

(51) Int. Cl.
*A61K 31/517*     (2006.01)
*A61P 35/00*      (2006.01)
*C07K 16/22*      (2006.01)

(52) U.S. Cl.
CPC .......... *A61K 31/517* (2013.01); *A61P 35/00* (2018.01); *C07K 16/22* (2013.01)

(58) Field of Classification Search
CPC .................................................. A61K 31/517
See application file for complete search history.

(56) References Cited

U.S. PATENT DOCUMENTS

| | | | |
|---|---|---|---|
| 6,884,879 B1 | 4/2005 | Baca et al. | |
| 12,016,862 B2 * | 6/2024 | Evangelista | A61K 39/3955 |
| 2018/0334454 A1 * | 11/2018 | Lanman | A61K 31/416 |
| 2020/0181118 A1 * | 6/2020 | Malhotra | C07D 405/14 |
| 2020/0222407 A1 | 7/2020 | Lipford et al. | |

FOREIGN PATENT DOCUMENTS

WO     2020/097537 A2     5/2020

OTHER PUBLICATIONS

He, R., et al., "Biologic therapies for advanced pancreatic cancer" Expert Rev Anticancer Ther 8(8):1331-1338 (Aug. 1, 2008).
"International Preliminary Report on Patentability—PCT/US2021/058877" (Report Issuance Date: May 16, 2023; Chapter I), :pp. 1-7 (May 25, 2023).
"International Search Report—PCT/US2021/058877" (w/Written Opinion), :pp. 1-10 (Feb. 18, 2022).
Tai, J., et al., "Tumor Shrinkage, Downregulation of in situ VEGF and K-Ras Expression, and Correlating Changes in CT Perfusion Parameters Following 6-Day Vandetanib Treatment in Hypovascular K-Ras Mutant LoVo Human Colon Tumor Xenografts" Poster (P287) Proceedings of the 2011 World Molecular Imaging Congress, San Diego, California US, pp. S270-S270 ( Sep. 7, 2011).

* cited by examiner

*Primary Examiner* — John S Kenyon
*Assistant Examiner* — Rehana Ismail
(74) *Attorney, Agent, or Firm* — Genentech, Inc.

(57)     ABSTRACT

Provided herein are combination therapies comprising a KRas$^{G12C}$ inhibitor (e.g. Compound 1 or a pharmaceutically acceptable salt thereof) and a VEGF antagonist (e.g., bevacizumab) and methods of using such combination therapies.

19 Claims, 2 Drawing Sheets

METHODS AND COMPOSITIONS COMPRISING A KRas$^{G12C}$ INHIBITOR AND A VEGF INHIBITOR FOR TREATING SOLID TUMORS

CROSS REFERENCE TO RELATED APPLICATIONS

This application is a Continuation Application of U.S. application Ser. No. 17/524,050, filed on Nov. 11, 2021, which claims priority to U.S. Provisional Patent Application No. 63/113,609, filed on Nov. 13, 2020, which is herein incorporated by reference in its entirety and for all purposes.

FIELD OF INVENTION

Provided herein are combination therapies comprising a KRas$^{G12C}$ inhibitor (e.g. Compound 1) and a VEGF antagonist (e.g., bevacizumab) and methods of using such combination therapies.

BACKGROUND

The Kirsten rat sarcoma viral oncogene homolog (KRAS) is a central component of the RAS/MAPK signal transduction pathway, an intracellular network of proteins that transmit extracellular growth factor signals to regulate cell proliferation, differentiation, and survival. Mutations in KRAS can result in alterations at several amino acids, including glycine 12 (G12), glycine 13, and glutamine 61, commonly found in solid tumors and associated with tumorigenesis and aggressive tumor growth (Der et al. Proc Natl Acad Sci USA 1982; 79:3637-40; Parada et al. Nature 1982; 297:474-8; Santos et al. Nature 1982; 298:343-7; Taparowsky et al. Nature 1982; 300:762-5; Capon et al. Nature 1983; 304: 507-13). Oncogenic KRAS mutations that result in the change from G12 to cysteine (G12C) are prevalent in non-small cell lung cancer (NSCLC) (~12%), colorectal cancer (CRC) (~4%), and other tumor types (≤4%) (Bailey et al. Nature 2016; 531:47-52; Campbell et al. Nat Genet 2016; 48:607-16; Giannakis et al. Cell Reports 2016; 15:857-65; Hartmaier et al. Genome Med 2017; 9(16); Jordan et al. Cancer Discov 2017; 7:596-609).

Advanced stage tumors harboring the KRas$^{G12C}$ mutation (hereafter referred to as KRas$^{G12C}$-positive tumors), including lung cancer (e.g. NSCLC), CRC, and other solid tumors such as hepatocellular carcinoma, breast cancer, renal cell carcinoma, endometrial cancer, ovarian cancer, and pancreatic cancer are incurable and carry a poor prognosis (Roman et al. Mol Cancer 2018; 17:33; Wan et al. World J Gastroenterol 2019; 25:808-23). In addition, patients with advanced stage KRas$^{G12C}$-positive cancers may derive limited benefit from select chemotherapies and targeted therapies, thus, restricting effective available treatment options (Roman et al. 2018).

Thus, there is a need for effective therapies and combination therapies for treating cancers such as lung cancer, colorectal cancer, hepatocellular carcinoma, breast cancer, renal cell carcinoma, endometrial cancer, ovarian cancer, and pancreatic cancer harboring KRas$^{G12C}$ mutations.

SUMMARY

Provided herein are solutions to these and other problems in the art.

In one aspect provided herein is a combination therapy comprising Compound 1 or a pharmaceutically acceptable salt thereof as described herein and an anti-VEGF antibody. In one such embodiment, the anti-VEGF antibody is bevacizumab. In another such embodiment, Compound 1 is an adipate salt thereof. In another such embodiment, Compound 1 or a pharmaceutically acceptable salt thereof is administered QD on days 1-21 of a first 21-day cycle and bevacizumab administered Q3W on day 1 of the first 21-day cycle. In still another embodiment, Compound 1 or a pharmaceutically acceptable salt thereof is administered QD at an amount of about 50 mg-500 mg on days 1-21 of a first 21-day cycle and bevacizumab is administered Q3W at an amount of about 5-20 mg/kg on day 1 of the first 21-day cycle. In one such embodiment, bevacizumab is administered Q3W at an amount of 15 mg/kg on day 1 of the first 21-day cycle.

In another aspect provided herein is a method of treating lung cancer mediated by a KRas$^{G12C}$ mutation in a patient having such a lung cancer, the method comprising administering an effective amount of a combination therapy comprising Compound 1 or a pharmaceutically acceptable salt thereof as described herein and an anti-VEGF antibody.

In another aspect provided herein is a method of treating colorectal cancer mediated by a KRas$^{G12C}$ mutation in a patient having such a lung cancer, the method comprising administering an effective amount of a combination therapy comprising Compound 1 or a pharmaceutically acceptable salt thereof as described herein and an anti-VEGF antibody.

In another aspect provided herein is a method of treating pancreatic cancer mediated by a KRas$^{G12C}$ mutation in a patient having such a lung cancer, the method comprising administering an effective amount of a combination therapy comprising Compound 1 or a pharmaceutically acceptable salt thereof as described herein and an anti-VEGF antibody.

In another aspect provided herein is a method of treating hepatocellular carcinoma, breast cancer, renal cell carcinoma, endometrial cancer, or ovarian cancer mediated by a KRas$^{G12C}$ mutation in a patient having such a lung cancer, the method comprising administering an effective amount of a combination therapy comprising Compound 1 or a pharmaceutically acceptable salt thereof as described herein and an anti-VEGF antibody.

In such embodiments of the methods, the anti-VEGF antibody is bevacizumab. In another such embodiment of the methods, Compound 1 is an adipate salt thereof. In another such embodiment of the methods, Compound 1 or a pharmaceutically acceptable salt thereof is administered QD on days 1-21 of a first 21-day cycle and bevacizumab administered Q3W on day 1 of the first 21-day cycle. In still another embodiment of the methods, Compound 1 or a pharmaceutically acceptable salt thereof is administered QD at an amount of about 50 mg-500 mg on days 1-21 of a first 21-day cycle and bevacizumab is administered Q3W at an amount of about 5-20 mg/kg on day 1 of the first 21-day cycle. In one such embodiment of the methods, bevacizumab is administered Q3W at an amount of 15 mg/kg on day 1 of the first 21-day cycle.

In another aspect provided herein is a method of treating NSCLC, CRC, or pancreatic cancer in a patient having such a cancer, the method comprising administering to the patient a treatment regimen comprising an effective amount of Compound 1 or a pharmaceutically acceptable salt thereof as described herein and an effective amount of an anti-VEGF antibody (e.g. bevacizumab).

In another aspect provided herein is a use of a combination therapy comprising Compound 1 or a pharmaceutically acceptable salt thereof and bevacizumab for the treatment of lung cancer, CRC, or pancreatic cancer as described herein.

In still another aspect provided herein is a use of a combination therapy comprising Compound 1 or a pharmaceutically acceptable salt thereof and bevacizumab for the manufacture of a medicament for the treatment of lung cancer, CRC, or pancreatic cancer

DETAILED DESCRIPTION

Definitions

Figure 1:
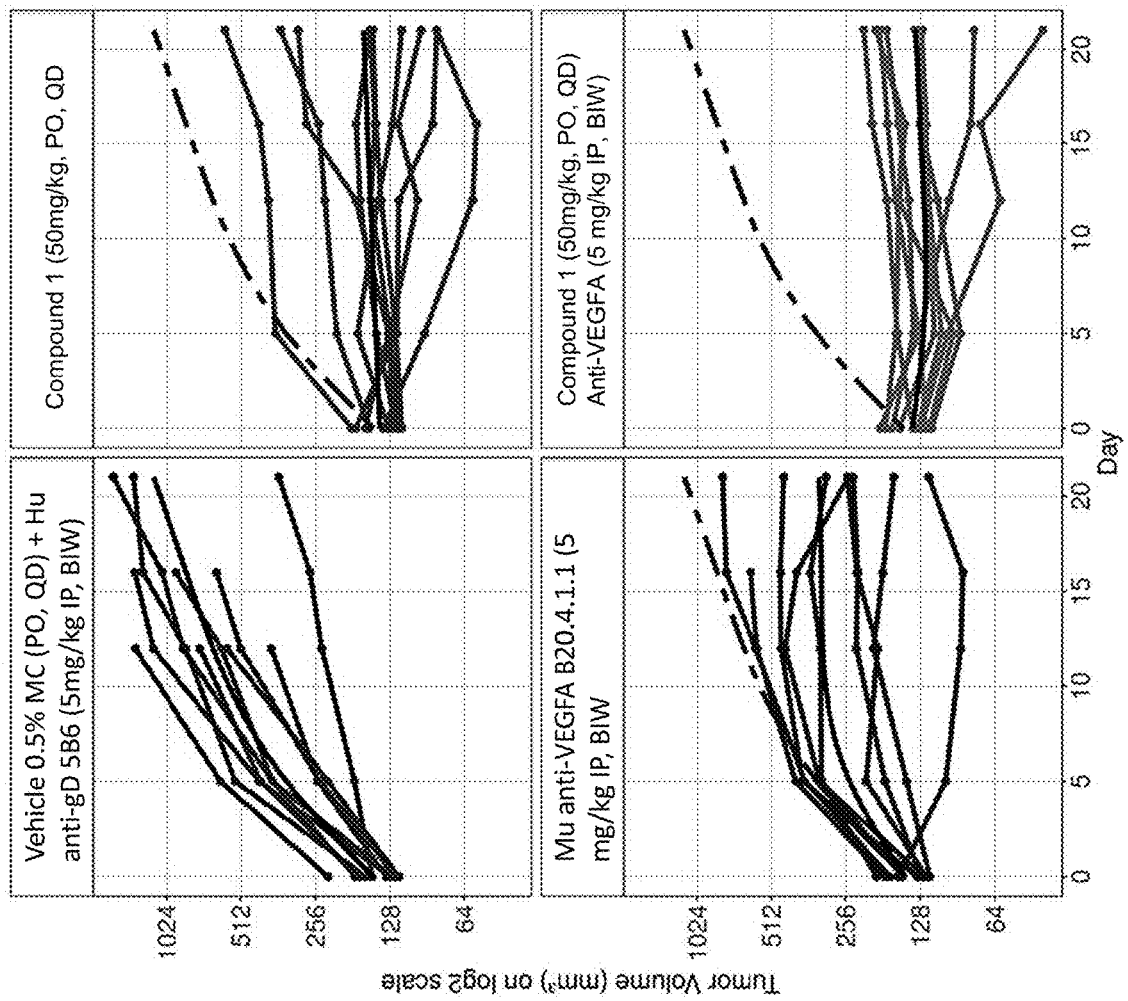
FIG. 1 illustrates the effect of Compound 1 (adipate salt) dosed alone at 50 mg/kg and in combination with anti-VEGF antibody in NCI-H2122 NSCLC tumor xenografts in nude mice. Vehicles=0.5% (w/v) methylcellulose. Individual tumor volume data is shown for Vehicle/anti-VEGF antibody control (upper left panel), anti-VEGF antibody (lower left panel), Compound 1 (upper right panel), and Compound 1+anti-VEGF antibody (lower right panel). Each group (n=10) was dosed for 21 days. Dose levels are expressed as free-base equivalents.

Unless defined otherwise, all technical and scientific terms used herein have the same meaning as commonly understood by those of ordinary skill in the art to which the invention belongs. See, e.g., Singleton et al., DICTIONARY OF MICROBIOLOGY AND MOLECULAR BIOLOGY 2nd ed., J. Wiley & Sons (New York, NY 1994); Sambrook et al., MOLECULAR CLONING, A LABORATORY MANUAL, Cold Springs Harbor Press (Cold Springs Harbor, NY 1989). Any methods, devices and materials similar or equivalent to those described herein can be used in the practice of this invention.

The following definitions are provided to facilitate understanding of certain terms used frequently herein and are not meant to limit the scope of the present disclosure. All references referred to herein are incorporated by reference in their entirety.

As used herein, and unless otherwise specified, the terms "about" and "approximately," when referring to doses, amounts, or weight percents of ingredients of a composition or a dosage form, mean a dose, amount, or weight percent that is recognized by one of ordinary skill in the art to provide a pharmacological effect equivalent to that obtained from the specified dose, amount, or weight percent. The equivalent dose, amount, or weight percent can be within 30%, 20%, 15%, 10%, 5%, 1%, or less of the specified dose, amount, or weight percent.

A "KRas$^{G12C}$ inhibitor" as used herein refers to a covalent inhibitor that specifically binds to a mutant KRas protein comprising a Gly to Cys mutation at a position corresponding to residue 12.

"Compound 1" refers to a compound having structure:

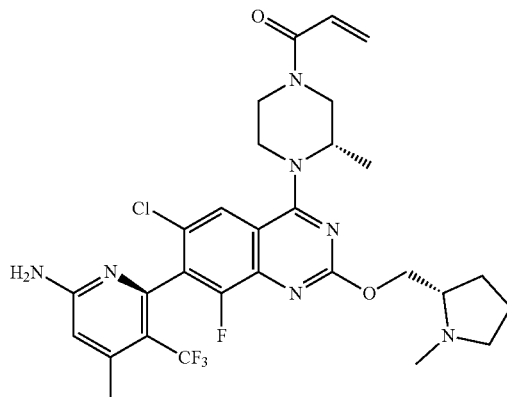

having the chemical name 1-((S)-4-((R)-7-(6-amino-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazin-1-yl)prop-2-en-1-one. In one embodiment, Compound 1 is an adipate salt.

The term "pharmaceutically acceptable" refers to molecular entities and compositions that do not produce an adverse, allergic or other untoward reaction when administered to an animal, such as, for example, a human, as appropriate.

Compounds of the invention may be in the form of a salt, such as a pharmaceutically acceptable salt. "Pharmaceutically acceptable salts" include both acid and base addition salts. "Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, malonic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, benzenesulfonic acid, p-toluenesulfonic acid, salicylic acid and the like. In one embodiment, the salt is formed with adipic acid.

The term "pharmaceutically acceptable base addition salts" include those derived from inorganic bases such as sodium, potassium, lithium, ammonium, calcium, magnesium, iron, zinc, copper, manganese, aluminum salts and the like. Particular base addition salts are the ammonium, potassium, sodium, calcium and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particular organic non-toxic bases include isopropylamine, diethylamine, ethanolamine, tromethamine, dicyclohexylamine, choline, and caffeine.

In some embodiments, a salt is selected from a hydrochloride, hydrobromide, trifluoroacetate, sulfate, phosphate, acetate, fumarate, maleate, tartrate, lactate, citrate, pyruvate, succinate, oxalate, methanesulfonate, p-toluenesulfonate, bisulfate, benzenesulfonate, ethanesulfonate, malonate, xinafoate, ascorbate, oleate, nicotinate, saccharinate, adipate, formate, glycolate, palmitate, L-lactate, D-lactate, aspartate, malate, L-tartrate, D-tartrate, stearate, furoate (e.g., 2-furoate or 3-furoate), napadisylate (naphthalene-1,5-disulfonate or naphthalene-1-(sulfonic acid)-5-sulfonate), edisylate (ethane-1,2-disulfonate or ethane-1-(sulfonic acid)-2-sulfonate), isothionate (2-hydroxyethylsulfonate), 2-mesitylenesulfonate, 2-naphthalenesulfonate, 2,5-dichlorobenzenesulfonate, D-mandelate, L-mandelate, cinnamate, benzoate, adipate, esylate, malonate, mesitylate (2-mesitylenesulfonate), napsylate (2-naphthalenesulfonate), camsylate (camphor-10-sulfonate, for example (1S)-(+)-10-camphorsulfonic acid salt), glutamate, glutarate, hippurate (2-(benzoylamino)acetate), orotate, xylate (p-xylene-2-sulfonate), and pamoic (2,2'-dihydroxy-1,1'-dinaphthylmethane-3,3'-dicarboxylate).

The terms "inhibiting" and "reducing," or any variation of these terms, includes any measurable decrease or complete inhibition to achieve a desired result. For example, there may be a decrease of about, at most about, or at least about 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, reduction of activity compared to normal.

The term "vascular endothelial growth factor" or "VEGF" refers to vascular endothelial growth factor protein A, as exemplified by Swiss Prot Accession Number P15692, Gene ID (NCBI): 7422. The term "VEGF" encompasses the protein having the amino acid sequence of Swiss Prot Accession Number P15692, Gene ID (NCBI): 7422 as well as homologues and isoforms thereof. The term "VEGF" also encompasses the known isoforms, e.g., splice isoforms, of VEGF, e.g., $VEGF_{111}$, $VEGF_{121}$, $VEGF_{145}$, $VEGF_{165}$, $VEGF_{189}$, and $VEGF_{206}$, together with the naturally-occurring allelic and processed forms thereof, including the 110 amino acid human vascular endothelial cell growth factor generated by plasmin cleavage of $VEGF_{165}$ as described in Ferrara *Mol. Biol. Cell.* 21:687, 2010; Leung et al., *Science*, 246:1306, 1989; and Houck et al., *Mol. Endocrin.*, 5:1806, 1991. The term "VEGF" also refers to VEGFs from non-human species such as mouse, rat or primate. Sometimes the VEGF from a specific species are indicated by terms such as hVEGF for human VEGF, mVEGF for murine VEGF, and the like. The term "VEGF" refers to truncated forms of the polypeptide comprising amino acids 8 to 109 or 1 to 109 of the 165-amino acid human vascular endothelial cell growth factor. Reference to any such forms of VEGF may be identified in the present application, e.g., by "$VEGF_{109}$," "VEGF (8-109)," "VEGF (1-109)" or "$VEGF_{165}$." The amino acid positions for a "truncated" native VEGF are numbered as indicated in the native VEGF sequence. For example, amino acid position 17 (methionine) in truncated native VEGF is also position 17 (methionine) in native VEGF. The truncated native VEGF has binding affinity for the KDR and Flt-1 receptors comparable to native VEGF. The term "VEGF variant" as used herein refers to a VEGF polypeptide, which includes one or more amino acid mutations in the native VEGF sequence. Optionally, the one or more amino acid mutations include amino acid substitution(s). For purposes of shorthand designation of VEGF variants described herein, it is noted that numbers refer to the amino acid residue position along the amino acid sequence of the putative native VEGF (provided in Leung et al., supra and Houck et al., supra). Unless specified otherwise, the term "VEGF" as used herein indicates VEGF-A.

A "VEGF antagonist" or "VEGF-specific antagonist" refers to a molecule capable of binding to VEGF, reducing VEGF expression levels, or neutralizing, blocking, inhibiting, abrogating, reducing, or interfering with VEGF biological activities, including, but not limited to, VEGF binding to one or more VEGF receptors, VEGF signaling, and VEGF mediated angiogenesis and endothelial cell survival or proliferation. For example, a molecule capable of neutralizing, blocking, inhibiting, abrogating, reducing, or interfering with VEGF biological activities can exert its effects by binding to one or more VEGF receptor (VEGFR) (e.g., VEGFR1, VEGFR2, VEGFR3, membrane-bound VEGF receptor (mbVEGFR), or soluble VEGF receptor (sVEGFR)). Included as VEGF-specific antagonists useful in the methods of the invention are polypeptides that specifically bind to VEGF, anti-VEGF antibodies and antigen-binding fragments thereof, receptor molecules and derivatives which bind specifically to VEGF thereby sequestering its binding to one or more receptors, fusions proteins (e.g., VEGF-Trap (Regeneron)), and $VEGF_{121}$-gelonin (Peregrine). VEGF-specific antagonists also include antagonist variants of VEGF polypeptides, antisense nucleobase oligomers complementary to at least a fragment of a nucleic acid molecule encoding a VEGF polypeptide; small RNAs complementary to at least a fragment of a nucleic acid molecule encoding a VEGF polypeptide; ribozymes that target VEGF; peptibodies to VEGF; and VEGF aptamers. VEGF antagonists also include polypeptides that bind to VEGFR, anti-VEGFR antibodies, and antigen-binding fragments thereof, and derivatives which bind to VEGFR thereby blocking, inhibiting, abrogating, reducing, or interfering with VEGF biological activities (e.g., VEGF signaling), or fusions proteins. VEGF-specific antagonists also include nonpeptide small molecules that bind to VEGF or VEGFR and are capable of blocking, inhibiting, abrogating, reducing, or interfering with VEGF biological activities. Thus, the term "VEGF activities" specifically includes VEGF mediated biological activities of VEGF. In certain embodiments, the VEGF antagonist reduces or inhibits, by at least 10%, 20%, 30%, 40%, 50%, 60%, 70%, 80%, 90% or more, the expression level or biological activity of VEGF. In some embodiments, the VEGF inhibited by the VEGF-specific antagonist is VEGF (8-109), VEGF (1-109), or $VEGF_{165}$.

An "anti-VEGF antibody" is an antibody that binds to VEGF with sufficient affinity and specificity. In certain embodiments, the antibody will have a sufficiently high binding affinity for VEGF, for example, the antibody may bind hVEGF with a $K_d$ value of between 100 nM-1 pM. Antibody affinities may be determined, e.g., by a surface plasmon resonance-based assay (such as the BIAcore® assay as described in PCT Application Publication No. WO2005/012359); enzyme-linked immunoabsorbent assay (ELISA); and competition assays (e.g. radioimmunoassays (RIAs)).

In certain embodiments, the anti-VEGF antibody can be used as a therapeutic agent in targeting and interfering with diseases or conditions wherein the VEGF activity is involved. Also, the antibody may be subjected to other biological activity assays, e.g., in order to evaluate its effectiveness as a therapeutic. Such assays are known in the art and depend on the target antigen and intended use for the antibody. Examples include the HUVEC inhibition assay; tumor cell growth inhibition assays (as described in WO 89/06692, for example); antibody-dependent cellular cytotoxicity (ADCC) and complement-mediated cytotoxicity (CDC) assays (U.S. Pat. No. 5,500,362); and agonistic activity or hematopoiesis assays (see WO 95/27062). An anti-VEGF antibody will usually not bind to other VEGF homologues such as VEGF-B or VEGF-C, nor other growth factors such as PlGF, PDGF, or bFGF. In one embodiment, anti-VEGF antibody is a monoclonal antibody that binds to the same epitope as the monoclonal anti-VEGF antibody A4.6.1 produced by hybridoma ATCC HB 10709. In another embodiment, the anti-VEGF antibody is a recombinant humanized anti-VEGF monoclonal antibody generated according to Presta et al. (*Cancer Res.* 57:4593-4599, 1997), including but not limited to the antibody known as bevacizumab (BV; AVASTIN®).

The anti-VEGF antibody "bevacizumab," also known as "rhuMAb VEGF," "BV," and marketed under the tradenames "AVASTIN®," "Zirabev®," and "Mvasi®" is a recombinant humanized anti-VEGF monoclonal antibody generated according to Presta et al. (*Cancer Res.* 57:4593-4599, 1997).

"Bevacizumab" comprises mutated human IgG1 framework regions and antigen-binding complementarity-determining regions from the murine anti-hVEGF monoclonal antibody A.4.6.1 that blocks binding of human VEGF to its receptors. Approximately 93% of the amino acid sequence of bevacizumab, including most of the framework regions, is derived from human IgG1, and about 7% of the sequence is derived from the murine antibody A4.6.1. Bevacizumab has a molecular mass of about 149,000 Daltons and is glycosylated. Bevacizumab and other humanized anti-VEGF antibodies are further described in U.S. Pat. No. 6,884,879, issued Feb. 26, 2005, the entire disclosure of which is expressly incorporated herein by reference. Additional preferred antibodies include the G6 or B20 series antibodies (e.g., G6-31, B20-4.1), as described in PCT Application Publication No. WO 2005/012359. For additional preferred antibodies see U.S. Pat. Nos. 7,060,269, 6,582,959, 6,703,020; 6,054,297; WO98/45332; WO 96/30046; WO94/10202; EP 0666868B1; U.S. Patent Application Publication Nos. 2006009360, 20050186208, 20030206899, 20030190317, 20030203409, and 20050112126; and Popkov et al., (*Journal of Immunological Methods* 288:149-164, 2004). Other preferred antibodies include those that bind to a functional epitope on human VEGF comprising of residues F17, M18, D19, Y21, Y25, Q89, 191, K101, E103, and C104 or, alternatively, comprising residues F17, Y21, Q22, Y25, D63, 183, and Q89. Bevacizumab is approved for the treatment of a number of different solid tumor types, including metastatic colorectal cancer, advanced NSCLC, metastatic breast cancer, advanced renal cell cancer, ovarian cancer, cervical cancer, unresectable or metastatic hepatocellular carcinoma, and recurrent glioblastoma.

The term "cancer" refers to a disease caused by an uncontrolled division of abnormal cells in a part of the body. In one embodiment, the cancer is lung cancer. In another embodiment, the cancer is NSCLC. In another embodiment, the cancer is colorectal cancer (e.g. metastatic CRC). In another embodiment, the cancer is pancreatic cancer. In still another embodiment, the cancer is hepatocellular carcinoma (e.g. unresectable or metastatic). In another embodiment, the cancer is breast cancer (e.g. metastatic breast cancer "mBC"). In still another embodiment, the cancer is renal cell carcinoma (e.g. advanced renal cell carcinoma). In another embodiment, the cancer is ovarian cancer. In still another embodiment, the cancer is endometrial cancer. "Cancer" as used herein, refers to cancer characterized as having a $KRas^{G12C}$ mutation.

As used herein, "treating" comprises treatment with an effective amount of a therapeutic agent (e.g., bevacizumab or Compound 1) or combination of therapeutic agents (e.g., bevacizumab and Compound 1). The treatment may be first-line treatment (e.g., the patient may be previously untreated or not have received prior systemic therapy), or second line or later treatment. For example, a patient is successfully "treated" if one or more symptoms associated with a cancer described herein are mitigated or eliminated, including, but are not limited to, reducing the proliferation of (or destroying) cancerous cells, decreasing symptoms resulting from the disease, increasing the quality of life of those suffering from the disease, decreasing the dose of other medications required to treat the disease, and/or prolonging survival of patients.

The term "delaying progression" of a disease refers to deferring, hindering, slowing, retarding, stabilizing, and/or postponing development of a cancer described herein. This delay can be of varying lengths of time, depending on the history of the cancer described herein and/or patient being treated. As is evident to one skilled in the art, a sufficient or significant delay can, in effect, encompass prevention, in that the patient does not develop the cancer.

Herein, an "effective amount" refers to the amount of a therapeutic agent described herein (e.g., bevacizumab and/or Compound 1) that achieves a therapeutic result. In some examples, the effective amount of a therapeutic agent or a combination of therapeutic agents is the amount of the agent or of the combination of agents that achieves a clinical endpoint as provided herein. An effective amount herein may vary according to factors such as the disease state, age, sex, and weight of the patient, and the ability of the agent to elicit a desired response in the patient. An effective amount is also one in which any toxic or detrimental effects of the treatment are outweighed by the therapeutically beneficial effects. In some embodiments, an effective amount of the drug may have the effect in reducing the number of cancer cells; reducing the tumor size; inhibiting (i.e., slow or stop) cancer cell infiltration into peripheral organs; inhibit (i.e., slow or stop) tumor metastasis; inhibiting (i.e., slow or stop) tumor growth; and/or relieving one or more of the symptoms associated with the disease. An effective amount can be administered in one or more administrations. An effective amount of drug, compound, pharmaceutical composition, or combination therapy described herein can be an amount sufficient to accomplish therapeutic treatment either directly or indirectly.

"Objective response rate" or "ORR" refers the percentage of patients with a confirmed complete response or partial response on two consecutive occasions≥4 weeks apart, as determined by the investigator according to RECIST v1.1.

"Duration of response" or "DOR" refers to the time from the first occurrence of a documented objective response to disease progression, as determined by the investigator according to RECIST v1.1, or death from any cause, whichever occurs first.

"Progression free survival" or "PFS" refers to the time from enrollment to the date of the first recorded occurrence of disease progression, as determined by the investigator using RECIST v1.1 or death from any cause, whichever occurs first.

As used herein, "complete response" and "CR" refers to disappearance of all target lesions and (if applicable) normalization of tumor marker level.

As used herein, "partial response" and "PR" refers to persistence of one or more non-target lesions and/or (if applicable) maintenance of tumor marker level above the normal limits. A PR can also refer to ≥30% decrease in sum of diameters of target lesions, in the absence of CR, new lesions, and unequivocal progression in non-target lesions.

An "administration period" or "cycle" refers to a period of time comprising administration of one or more agents described herein (e.g. Compound 1 and bevacizumab) and an optional period of time comprising no administration of one or more of the agents described herein. For example, a cycle can be 21 days in total and include administration of one or more agents described herein (e.g. Compound 1 and bevacizumab) each day of the cycle. In another example, a cycle can be 28 days in total length and include administration of one or more agents described herein (e.g. Compound 1 and bevacizumab) for 21 days and a rest period of 7 days. A "rest period" refers to a period of time where at least one of the agents described herein (i.e. Compound 1 and bevacizumab) are not administered. In one embodiment, a rest period refers to a period of time where none of the agents described herein (i.e. Compound 1 and bevacizumab) are administered. A rest period as provided herein can in some instances include administration of another agent that is not Compound 1 or bevacizumab. In such instances, administration of another agent during a rest period should not interfere or detriment administration of an agent described herein. In one instance, cycle as used herein refers to 21 day cycles without a rest period.

A "dosing regimen" refers to an administration period of the agents described herein comprising one or more cycles, where each cycle can include administration of the agents described herein at different times or in different amounts.

"QD" refers to administration of an agent described herein once daily.

"BID" refers to administration of an agent described herein twice daily.

"Q3W" refers to administration of an agent described herein once every three weeks.

"PO" refers to oral administration of an agent described herein.

"IV" refers to intravenous administration of any agent described herein.

A graded adverse event refers to the severity grading scale as established for by NCI CTCAE. In one embodiment, the adverse event is graded in accordance with the table below.

| Grade | Severity |
| --- | --- |
| 1 | Mild; asymptomatic or mild symptoms; clinical or diagnostic observations only; or intervention not indicated |
| 2 | Moderate; minimal, local, or non-invasive intervention indicated; or limiting age-appropriate instrumental activities of daily living[a] |
| 3 | Severe or medically significant, but not immediately life-threatening; hospitalization or prolongation of hospitalization indicated; disabling; or limiting self-care activities of daily living[b, c] |
| 4 | Life-threatening consequences or urgent intervention indicated[d] |
| 5 | Death related to adverse event[d] |

The term "patient" refers to a human patient. A patient may be an adult.

The term "antibody" herein specifically covers monoclonal antibodies (including full-length monoclonal antibodies), polyclonal antibodies, multispecific antibodies (e.g., bispecific antibodies), and antibody fragments so long as they exhibit the desired biological activity. In one instance, the antibody is a full-length monoclonal antibody.

The term IgG "isotype" or "subclass" as used herein is meant any of the subclasses of immunoglobulins defined by the chemical and antigenic characteristics of their constant regions.

Depending on the amino acid sequences of the constant domains of their heavy chains, antibodies (immunoglobulins) can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, γ, ε, γ, and μ, respectively. The subunit structures and three-dimensional configurations of different classes of immunoglobulins are well known and described generally in, for example, Abbas et al. Cellular and Mol. Immunology, 4th ed. (W.B. Saunders, Co., 2000). An antibody may be part of a larger fusion molecule, formed by covalent or non-covalent association of the antibody with one or more other proteins or peptides.

The terms "full-length antibody," "intact antibody," and "whole antibody" are used herein interchangeably to refer to an antibody in its substantially intact form, not antibody fragments as defined below. The terms refer to an antibody comprising an Fc region.

The term "Fc region" herein is used to define a C-terminal region of an immunoglobulin heavy chain that contains at least a portion of the constant region. The term includes native sequence Fc regions and variant Fc regions. In one aspect, a human IgG heavy chain Fc region extends from Cys226, or from Pro230, to the carboxyl-terminus of the heavy chain. However, antibodies produced by host cells may undergo post-translational cleavage of one or more, particularly one or two, amino acids from the C-terminus of the heavy chain. Therefore, an antibody produced by a host cell by expression of a specific nucleic acid molecule encoding a full-length heavy chain may include the full-length heavy chain, or it may include a cleaved variant of the full-length heavy chain. This may be the case where the final two C-terminal amino acids of the heavy chain are glycine (G446) and lysine (K447). Therefore, the C-terminal lysine (Lys447), or the C-terminal glycine (Gly446) and lysine (Lys447), of the Fc region may or may not be present. Amino acid sequences of heavy chains including an Fc region are denoted herein without the C-terminal lysine (Lys447) if not indicated otherwise. In one aspect, a heavy chain including an Fc region as specified herein, comprised in an antibody disclosed herein, comprises an additional C-terminal glycine-lysine dipeptide (G446 and K447). In one aspect, a heavy chain including an Fc region as specified herein, comprised in an antibody disclosed herein, comprises an additional C-terminal glycine residue (G446). In one aspect, a heavy chain including an Fc region as specified herein, comprised in an antibody disclosed herein, comprises an additional C-terminal lysine residue (K447). In one embodiment, the Fc region contains a single amino acid substitution N297A of the heavy chain. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, MD, 1991.

A "naked antibody" refers to an antibody that is not conjugated to a heterologous moiety (e.g., a cytotoxic moiety) or radiolabel. The naked antibody may be present in a pharmaceutical composition.

"Antibody fragments" comprise a portion of an intact antibody, preferably comprising the antigen-binding region thereof. In some instances, the antibody fragment described herein is an antigen-binding fragment. Examples of antibody fragments include Fab, Fab', F(ab')$_2$, and Fv fragments; diabodies; linear antibodies; single-chain antibody molecules (e.g., scFvs); and multispecific antibodies formed from antibody fragments.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies in accordance with the present invention may be made by a variety of techniques, including but not limited to the hybridoma method, recombinant DNA methods, phage-display methods, and methods utilizing transgenic animals containing all or part of the human immunoglobulin loci.

The term "hypervariable region" or "HVR" as used herein refers to each of the regions of an antibody variable domain which are hypervariable in sequence and which determine antigen binding specificity, for example "complementarity determining regions" ("CDRs").

Generally, antibodies comprise six CDRs: three in the VH (CDR-H1, CDR-H2, CDR-H3), and three in the VL (CDR-L1, CDR-L2, CDR-L3). Exemplary CDRs herein include:
  (a) hypervariable loops occurring at amino acid residues 26-32 (L1), 50-52 (L2), 91-96 (L3), 26-32 (H1), 53-55 (H2), and 96-101 (H3) (Chothia and Lesk, J. Mol. Biol. 196:901-917 (1987));
  (b) CDRs occurring at amino acid residues 24-34 (L1), 50-56 (L2), 89-97 (L3), 31-35b (H1), 50-65 (H2), and 95-102 (H3) (Kabat et al., Sequences of Proteins of Immunological Interest, 5th Ed. Public Health Service, National Institutes of Health, Bethesda, MD (1991)); and
  (c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)).

Unless otherwise indicated, the CDRs are determined according to Kabat et al., supra. One of skill in the art will understand that the CDR designations can also be determined according to Chothia, supra, McCallum, supra, or any other scientifically accepted nomenclature system.

"Framework" or "FR" refers to variable domain residues other than complementary determining regions (CDRs). The FR of a variable domain generally consists of four FR domains: FR1, FR2, FR3, and FR4. Accordingly, the CDR and FR sequences generally appear in the following sequence in VH (or VL): FR1-CDR-H1(CDR-L1)-FR2-CDR-H2(CDR-L2)-FR3-CDR-H3(CDR-L3)-FR4.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g., residues 82a, 82b, and 82c, etc., according to Kabat) after heavy chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g., Kabat et al., Sequences of Immunological Interest. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody.

The term "package insert" is used to refer to instructions customarily included in commercial packages of therapeutic products, that contain information about the indications, usage, dosage, administration, combination therapy, contraindications and/or warnings concerning the use of such therapeutic products.

As used herein, "in combination with" refers to administration of one treatment modality in addition to another treatment modality, for example, a treatment regimen that includes administration of a VEGF antagonist described herein (e.g., bevacizumab) and Compound 1 or a pharmaceutically acceptable salt thereof. As such, "in combination with" refers to administration of one treatment modality before, during, or after administration of the other treatment modality to the patient.

A drug that is administered "concurrently" with one or more other drugs is administered during the same treatment cycle, on the same day of treatment, as the one or more other drugs, and, optionally, at the same time as the one or more other drugs. For instance, for cancer therapies given every 3 weeks, the concurrently administered drugs are each administered on day 1 of a 3 week cycle.

Combination Therapies

Provided herein are combination therapies (compositions) comprising Compound 1 or a pharmaceutically acceptable salt thereof (e.g. Compound 1 adipate) and an anti-VEGF antagonist described herein. Further provided herein are combination therapies (compositions) comprising Compound 1 or a pharmaceutically acceptable salt thereof (e.g. Compound 1 adipate) and an anti-VEGF antibody (e.g. bevacizumab).

A variety of anti-VEGF antibodies are contemplated and described herein. In some instances, the anti-VEGF antibody is a monoclonal antibody. In some instances, the anti-VEGF antibody is an antibody fragment selected from the group consisting of Fab, Fab'-SH, Fv, scFv, and (Fab')2 fragments. In some instances, the anti-VEGF antibody is a humanized antibody. In some instances, the anti-VEGF antibody is a human antibody. In one embodiment, the anti-VEGF is bevacizumab (e.g. AVASTIN®, ZIRABEV® (bevacizumab-bvzr), or MVASI® (bevacizumab-awwb)).

In one aspect provided herein is a combination therapy comprising Compound 1 or a pharmaceutically acceptable salt thereof (e.g. Compound 1 adipate) and bevacizumab. In one embodiment, the combination therapies described herein are useful in the treatment of certain solid tumors comprising KRas$^{G12C}$ mutations. In one embodiment, the combination therapies described herein are useful in the treatment of certain types of lung cancer as described herein comprising KRas$^{G12C}$ mutations. In one such embodiment, the lung cancer is non-small cell lung cancer (NSCLC) comprising KRas$^{G12C}$ mutations. In another embodiment, the combination therapies described herein are useful in the treatment of colorectal cancer comprising KRas$^{G12C}$ mutations. In another embodiment, the combination therapies described herein are useful in the treatment of pancreatic cancer comprising KRas$^{G12C}$ mutations.

In another embodiment, the combination therapies described herein are useful in the treatment of hepatocellular carcinoma comprising KRas$^{G12C}$ mutations. In another embodiment, the combination therapies described herein are useful in the treatment of breast cancer comprising KRas$^{G12C}$ mutations. In another embodiment, the combination therapies described herein are useful in the treatment of renal cell carcinoma comprising KRas$^{G12C}$ mutations. In another embodiment, the combination therapies described herein are useful in the treatment of endometrial cancer comprising KRas$^{G12C}$ mutations. In another embodiment, the combination therapies described herein are useful in the treatment of ovarian cancer comprising KRas$^{G12C}$ mutations.

In one aspect provided herein is a combination therapy comprising Compound 1 or a pharmaceutically acceptable salt thereof administered QD on days 1-21 of a first 21-day cycle and an anti-VEGF antibody. In such embodiments, the combination therapies are useful in the treatment of a solid tumor comprising KRas$^{G12C}$ mutations as described herein (e.g. lung cancer, colorectal cancer, pancreatic cancer).

In one aspect provided herein is a combination therapy comprising Compound 1 or a pharmaceutically acceptable salt thereof administered QD on days 1-21 of a first 21-day cycle and bevacizumab administered Q3W on day 1 of the first 21-day cycle.

In one embodiment of the combination therapies described herein, Compound 1 or a pharmaceutically acceptable salt thereof is administered as a fixed dose QD administration. In one embodiment, the administration is oral (PO), where Compound 1 or a pharmaceutically acceptable salt thereof is formulated as a tablet or capsule. In one such embodiment, Compound 1 or a pharmaceutically acceptable salt thereof is formulated (and administered) as a film coated tablet.

In one embodiment of the combination therapies described herein, Compound 1 or a pharmaceutically acceptable salt thereof is administered at an amount of about 5 mg-600 mg, 5 mg-500 mg, 5 mg-400 mg, 5 mg-300 mg, 5 mg-250 mg, 5 mg-200 mg, 5 mg-150 mg, 5 mg-100 mg, 5 mg-50 mg, 5 mg-25 mg, 25 mg-600 mg, 25 mg-500 mg, 25 mg-400 mg, 25 mg-300 mg, 25 mg-250 mg, 25 mg-200 mg, 25 mg-150 mg, 25 mg-100 mg, 25 mg-50 mg, 50 mg-600 mg, 50 mg-500 mg, 50 mg-400 mg, 50 mg-300 mg, 50 mg-250 mg, 50 mg-200 mg, 50 mg-150 mg, or 50 mg-100 mg QD. In another embodiment, Compound 1 or a pharmaceutically acceptable salt thereof is administered at an amount of about 5 mg, 25 mg, 50 mg, 100 mg, 150 mg, 200 mg, 250 mg, 300 mg, 400 mg or 500 mg. In another embodiment, Compound 1 or a pharmaceutically acceptable salt thereof is administered at an amount of about 50 mg, 100 mg, 200 mg, 300 mg, or 400 mg. In still another embodiment, Compound 1 or a pharmaceutically acceptable salt thereof is administered at an amount of about 50 mg, 100 mg, or 400 mg. In one preferred embodiment, Compound 1 of the combination therapies described herein is administered as an adipate salt. In such embodiments, the amount of Compound 1 or a pharmaceutically acceptable salt thereof is administered as an amount relative to the free-base form. In one embodiment, Compound 1 or a pharmaceutically acceptable salt thereof is administered BID at an amount described herein (e.g. 50 mg, 100 mg, 200 mg, 300 mg, or 400 mg).

In one embodiment of the combination therapy described herein, the anti-VEGF antibody is administered in accordance with a package insert. In a preferred embodiment, the anti-VEGF antibody is bevacizumab. In one such embodiment, bevacizumab is administered according to the package insert at a fixed dose of 15 mg/kg. In one such embodiment, bevacizumab is administered over 90 min±15 min.

As a general proposition, the effective amount of an anti-VEGF antibody (e.g., bevacizumab) administered to a human will be in the range of about 1 to about 50 mg/kg of patient body weight, whether by one or more administrations.

In some exemplary embodiments, the anti-VEGF antibody is administered in a dose of about 1 to about 45 mg/kg, about 1 to about 40 mg/kg, about 1 to about 35 mg/kg, about 1 to about 30 mg/kg, about 1 to about 25 mg/kg, about 1 to about 20 mg/kg, about 1 to about 15 mg/kg, about 1 to about 10 mg/kg, about 1 to about 5 mg/kg, or about 5 to about 15 mg/kg administered daily, weekly, every two weeks, every three weeks, or every four weeks, for example. In one such embodiment, the anti-VEGF antibody is administered in a dose of about 5 mg/kg to about 15 mg/kg every 2 or every 3 weeks. In another such embodiment, the anti-VEGF antibody is administered in a dose of about 10 mg/kg to about 20 mg/kg every 2 or every 3 weeks.

In one embodiment, the anti-VEGF antibody is administered in a dose of about 15 mg/kg every 3 weeks (Q3W). In another embodiment, the anti-VEGF antibody is administered in a dose of about 10 mg/kg every 2 weeks (Q2W). In such embodiments, the anti-VEGF antibody is bevacizumab.

In one preferred embodiment, the combination therapies described herein comprise Compound 1 or a pharmaceutically acceptable salt thereof as described herein administered QD and bevacizumab, where bevacizumab is administered to the patient intravenously at a dose of about 15 mg/kg Q3W.

In one embodiment, the combination therapies described herein are used for treating lung cancer comprising a KRas$^{G12C}$ mutation. In one particular embodiment, the combination therapy comprises Compound 1 or a pharmaceutically acceptable salt thereof (e.g. Compound 1 adipate) and bevacizumab, where the combination therapy is for treating lung cancer comprising a KRas$^{G12C}$ mutation as described herein. In one such embodiment, the lung cancer is non-small cell lung carcinoma (NSCLC). In another such embodiment, the lung cancer is adenocarcinoma, squamous-cell lung carcinoma or large-cell lung carcinoma. The lung cancer can be stage I or II lung cancer. In one embodiment, the lung cancer is stage III or IV lung cancer.

In another aspect provided herein is a combination therapy useful in the treatment of lung cancer comprising a KRas$^{G12C}$ mutation where the combination therapy comprises Compound 1 or a pharmaceutically acceptable salt thereof (e.g. Compound 1 adipate) and bevacizumab. In one such embodiment, the lung cancer is NSCLC.

In still another aspect provided herein is a combination therapy useful in the treatment of lung cancer comprising a KRas$^{G12C}$ mutation where the combination therapy comprises Compound 1 or a pharmaceutically acceptable salt thereof (e.g. Compound 1 adipate) where Compound 1 or a pharmaceutically acceptable salt thereof is administered QD on days 1-21 of a first 21-day cycle and bevacizumab is administered Q3W on day 1 of the first 21-day cycle. In one preferred embodiment, the lung cancer is NSCLC.

In still another aspect provided herein is a combination therapy useful in the treatment of lung cancer comprising a KRas$^{G12C}$ mutation where the combination therapy comprises Compound 1 or a pharmaceutically acceptable salt thereof (e.g. Compound 1 adipate) where Compound 1 or a pharmaceutically acceptable salt thereof is administered QD at an amount of about 50 mg-500 mg on days 1-21 of a first 21-day cycle and bevacizumab is administered Q3W at an amount of about 15 mg/kg on day 1 of the first 21-day cycle. In one preferred embodiment, the lung cancer is NSCLC. In one embodiment, bevacizumab is administered according to a package insert.

In such embodiments where the combination is useful for the treatment of lung cancer comprising a KRas$^{G12C}$ mutation as described herein, the combination therapy can further comprise administration of one or both of carboplatin and paclitaxel.

In one embodiment, the combination therapies described herein are used for treating CRC comprising a KRas$^{G12C}$ mutation. In one particular embodiment, the combination therapy comprises Compound 1 or a pharmaceutically acceptable salt thereof (e.g. Compound 1 adipate) and bevacizumab, where the combination therapy is for treating CRC comprising a KRas$^{G12C}$ mutation as described herein. In one such embodiment, the CRC is metastatic CRC (mCRC). In one embodiment, the combination therapy is for first-line use treatment of CRC comprising a KRas$^{G12C}$ mutation. In another embodiment, the combination therapy is for second-line treatment of CRC comprising a KRas$^{G12C}$ mutation. In one such embodiment, the patient has previously progressed disease having had bevacizumab as a first-line therapy.

In still another aspect provided herein is a combination therapy useful in the treatment of CRC comprising a KRas$^{G12C}$ mutation where the combination therapy comprises Compound 1 or a pharmaceutically acceptable salt thereof (e.g. Compound 1 adipate) where Compound 1 or a pharmaceutically acceptable salt thereof is administered QD at an amount of about 50 mg-500 mg on days 1-21 of a first 21-day cycle and bevacizumab is administered Q3W at an amount of about 15 mg/kg on day 1 of the first 21-day cycle.

In such embodiments where the combination therapy is useful in the treatment of CRC comprising a KRas$^{G12C}$ mutation, such combination therapies can further comprise administration of fluoropyrimidine-irinotecan or fluoropyrimidine-oxaliplatin based chemotherapy.

In one embodiment, the combination therapies described herein are used for treating pancreatic cancer comprising a KRas$^{G12C}$ mutation. In one particular embodiment, the combination therapy comprises Compound 1 or a pharmaceutically acceptable salt thereof (e.g. Compound 1 adipate) and bevacizumab, where the combination therapy is for treating pancreatic cancer comprising a KRas$^{G12C}$ mutation as described herein.

In still another aspect provided herein is a combination therapy useful in the treatment of pancreatic cancer comprising a KRas$^{G12C}$ mutation where the combination therapy comprises Compound 1 or a pharmaceutically acceptable salt thereof (e.g. Compound 1 adipate) where Compound 1 or a pharmaceutically acceptable salt thereof is administered QD on days 1-21 of a first 21-day cycle and bevacizumab is administered Q3W on day 1 of the first 21-day cycle.

In still another aspect provided herein is a combination therapy useful in the treatment of pancreatic cancer comprising a KRas$^{G12C}$ mutation where the combination therapy comprises Compound 1 or a pharmaceutically acceptable salt thereof (e.g. Compound 1 adipate) where Compound 1 or a pharmaceutically acceptable salt thereof is administered QD at an amount of about 50 mg-500 mg on days 1-21 of a first 21-day cycle and bevacizumab is administered Q3W at an amount of about 5-20 mg/kg on day 1 of the first 21-day cycle. In one such embodiment, bevacizumab is administered at an amount of about 15 mg/kg Q3W as described herein. In one embodiment, bevacizumab is administered according to a package insert.

In still another aspect provided herein is a combination therapy useful in the treatment of hepatocellular carcinoma, breast cancer, renal cell carcinoma, endometrial cancer, or ovarian cancer comprising a KRas$^{G12C}$ mutation where the combination therapy comprises Compound 1 or a pharmaceutically acceptable salt thereof (e.g. Compound 1 adipate) where Compound 1 or a pharmaceutically acceptable salt thereof is administered QD at an amount of about 50 mg-500 mg on days 1-21 of a first 21-day cycle and bevacizumab is administered Q3W at an amount of about 5-20 mg/kg on day 1 of the first 21-day cycle. In one such embodiment, bevacizumab is administered at an amount of about 15 mg/kg Q3W as described herein. In one embodiment, bevacizumab is administered according to a package insert.

Methods of Treatment

Also provided herein are methods of treating a solid tumor comprising a KRas$^{G12C}$ mutation in a patient having such a solid tumor described herein (e.g. lung cancer, CRC, pancreatic cancer, hepatocellular carcinoma, breast cancer, renal cell carcinoma, endometrial cancer, or ovarian cancer). In one embodiment, is a method of treating lung cancer, CRC, pancreatic cancer, hepatocellular carcinoma, breast cancer, renal cell carcinoma, endometrial cancer, or ovarian cancer comprising a KRas$^{G12C}$ mutation in a patient having such a solid tumor, the method comprising administering to the patient an effective amount of a combination therapy comprising Compound 1 or a pharmaceutically acceptable salt thereof (e.g. Compound 1 adipate) and an anti-VEGF antibody described herein (e.g. bevacizumab).

In one aspect provided herein is a method of treating lung cancer comprising a KRas$^{G12C}$ mutation in a patient having such a lung cancer, the method comprising administering to the patient an effective amount of a combination therapy comprising Compound 1 or a pharmaceutically acceptable salt thereof (e.g. Compound 1 adipate) and an anti-VEGF antibody described herein. In one aspect provided herein is a method of treating lung cancer mediated by a KRas$^{G12C}$ mutation in a patient having such a lung cancer, the method comprising administering to the patient an effective amount of a combination therapy comprising Compound 1 or a pharmaceutically acceptable salt thereof (e.g. Compound 1 adipate) and bevacizumab.

In one embodiment of the methods provided herein, the lung cancer is non-small cell lung carcinoma (NSCLC). In one such embodiment, the anti-VEGF antibody is bevacizumab. In another embodiment of the methods provided herein, the lung cancer is adenocarcinoma, squamous-cell lung carcinoma or large-cell lung carcinoma. In one such embodiment, the cancer is lung adenocarcinoma. In another such embodiment, the lung cancer is a small cell lung carcinoma. In another embodiment, the lung cancer is small cell lung carcinoma. In still another embodiment, the lung cancer is glandular tumors, carcinoid tumors or undifferentiated carcinomas. The lung cancer can be stage I or II lung cancer. In one embodiment, the lung cancer is stage III or IV lung cancer.

Also provided herein is a method of treating NSCLC comprising a KRas$^{G12C}$ mutation in a patient having such a cancer, where the method comprises administering to the patient an effective amount of a combination therapy as described herein comprising a dosing regimen comprising: (i) administering an effective amount of Compound 1 or a pharmaceutically acceptable salt thereof QD on days 1-21 of a first 21-day cycle; and (ii) administering an effective amount of bevacizumab Q3W on day 1 of the first 21-day cycle. In one embodiment of the method provided herein, the method is for treating adenocarcinoma. In one embodiment of the method provided herein, the method comprises 2 or more cycles. In one such embodiment, the method is for treating first-line NSCLC.

Also provided herein is a method of treating NSCLC comprising a KRas$^{G12C}$ mutation in a patient having such a cancer, where the method comprises administering to the patient an effective amount of a combination therapy as described herein comprising a dosing regimen comprising: (i) administering 50 mg-500 mg of Compound 1 or a pharmaceutically acceptable salt thereof QD on days 1-21 of a first 21-day cycle; and (ii) administering about 5-20 mg/kg of bevacizumab Q3W on day 1 of the first 21-day cycle.

In one embodiment of the methods of treating lung cancer comprising a KRas$^{G12C}$ mutation as described herein, the method further comprises administering to the patient of an effective amount of one or both of carboplatin and paclitaxel.

In another aspect provided herein is a method treating CRC comprising a KRas$^{G12C}$ mutation in a patient having CRC, the method comprising administering to the patient an effective amount of a combination therapy comprising Compound 1 or a pharmaceutically acceptable salt thereof (e.g. Compound 1 adipate) and an anti-VEGF antibody described herein. In another embodiment of the methods provided herein is a method of treating CRC, the method comprising administering to the patient an effective amount of a combination therapy comprising Compound 1 or a pharmaceutically acceptable salt thereof (e.g. Compound 1 adipate) and bevacizumab.

Also provided herein is a method of treating CRC comprising a KRas$^{G12C}$ mutation in a patient having such a cancer, where the method comprises administering to the patient an effective amount of a combination therapy as described herein comprising a dosing regimen comprising: (i) administering an effective amount of Compound 1 or a pharmaceutically acceptable salt thereof QD on days 1-21 of a first 21-day cycle; and (ii) administering an effective amount of bevacizumab Q3W on day 1 of the first 21-day cycle. In one such embodiment, bevacizumab is administered at an amount of about 5-20 mg/kg as described herein. In another such embodiment, Compound 1 or a pharmaceutically acceptable salt thereof is administered at an amount of about 50 mg-500 mg as described herein. In one embodiment, bevacizumab is administered at an amount of 15 mg/kg.

In one embodiment of such methods for treating CRC comprising a KRas$^{G12C}$ mutation, such methods further comprise administering to the patient an effective amount of fluoropyrimidine-irinotecan or fluoropyrimidine-oxaliplatin based chemotherapy.

Also provided herein is a method of treating pancreatic cancer comprising a KRas$^{G12C}$ mutation in a patient having pancreatic cancer, the method comprising administering to the patient an effective amount of a combination therapy comprising Compound 1 or a pharmaceutically acceptable salt thereof (e.g. Compound 1 adipate) and an anti-VEGF antibody described herein. In another embodiment of the methods provided herein is a method of treating pancreatic cancer, the method comprising administering to the patient an effective amount of a combination therapy comprising Compound 1 or a pharmaceutically acceptable salt thereof (e.g. Compound 1 adipate) and bevacizumab.

In another embodiment, is a method of treating pancreatic cancer comprising a KRas$^{G12C}$ mutation in a patient having such a cancer, where the method comprises administering to the patient an effective amount of a combination therapy as described herein comprising a dosing regimen comprising: (i) administering an effective amount of Compound 1 or a pharmaceutically acceptable salt thereof QD on days 1-21 of a first 21-day cycle; and (ii) administering an effective amount of bevacizumab Q3W on day 1 of the first 21-day cycle. In one such embodiment, bevacizumab is administered at an amount of about 5 mg/kg-20 mg/kg as described herein. In one embodiment, bevacizumab is administered at an amount of 15 mg/kg. In another such embodiment, Compound 1 or a pharmaceutically acceptable salt thereof is administered at an amount of about 50 mg-500 mg as described herein.

Also provided herein is a method of treating hepatocellular carcinoma, breast cancer, renal cell carcinoma, endometrial cancer, or ovarian cancer comprising a KRas$^{G12C}$ mutation in a patient having such a cancer, the method comprising administering to the patient an effective amount of a combination therapy comprising Compound 1 or a pharmaceutically acceptable salt thereof (e.g. Compound 1 adipate) and an anti-VEGF antibody described herein. In another embodiment of the methods provided herein is a method of treating hepatocellular carcinoma, breast cancer, renal cell carcinoma, endometrial cancer, or ovarian cancer in a patient having such a cancer, the method comprising administering an effective amount of a combination therapy comprising Compound 1 or a pharmaceutically acceptable salt thereof (e.g. Compound 1 adipate) and bevacizumab.

In another embodiment, is a method of treating hepatocellular carcinoma, breast cancer, renal cell carcinoma, endometrial cancer, or ovarian cancer comprising a KRas$^{G12C}$ mutation in a patient having such a cancer, where the method comprises administering to the patient an effective amount of a combination therapy as described herein comprising a dosing regimen comprising: (i) administering an effective amount of Compound 1 or a pharmaceutically acceptable salt thereof QD on days 1-21 of a first 21-day cycle; and (ii) administering an effective amount of bevacizumab Q3W on day 1 of the first 21-day cycle. In one such embodiment, bevacizumab is administered at an amount of about 10 mg-20 mg as described herein. In one embodiment, bevacizumab is administered at an amount of 15 mg/kg. In another such embodiment, Compound 1 or a pharmaceutically acceptable salt thereof is administered at an amount of about 50 mg-500 mg as described herein.

In one embodiment of the methods described herein, Compound 1 or a pharmaceutically acceptable salt thereof is administered as a fixed dose QD administration. In one embodiment, the administration is oral (PO), where Compound 1 or a pharmaceutically acceptable salt thereof is formulated as a tablet or capsule. In one embodiment, Compound 1 or a pharmaceutically acceptable salt thereof is administered at an amount of 5 mg-600 mg, 5 mg-500 mg, 5 mg-400 mg, 5 mg-300 mg, 5 mg-250 mg, 5 mg-200 mg, 5 mg-150 mg, 5 mg-100 mg, 5 mg-50 mg, 5 mg-25 mg, 25 mg-600 mg, 25 mg-500 mg, 25 mg-400 mg, 25 mg-300 mg, 25 mg-250 mg, 25 mg-200 mg, 25 mg-150 mg, 25 mg-100 mg, 25 mg-50 mg, 50 mg-600 mg, 50 mg-500 mg, 50 mg-400 mg, 50 mg-300 mg, 50 mg-250 mg, 50 mg-200 mg, 50 mg-150 mg, or 50 mg-100 mg QD. In another embodiment, Compound 1 or a pharmaceutically acceptable salt thereof is administered at an amount of about 5 mg, 25 mg, 50 mg, 100 mg, 150 mg, 200 mg, 250 mg, 300 mg, 400 mg or 500 mg. In another embodiment, Compound 1 or a pharmaceutically acceptable salt thereof is administered at an amount of about 50 mg, 100 mg, 200 mg, 300 mg, or 400 mg. In still another embodiment, Compound 1 or a pharmaceutically acceptable salt thereof is administered at an amount of about 50 mg, 100 mg, or 400 mg. In one preferred embodiment, Compound 1 or a pharmaceutically acceptable salt thereof of the combination therapies described herein is administered as an adipate salt. In such embodiments, the amount of Compound 1 or a pharmaceutically acceptable salt thereof is administered as an amount relative to the free-base form.

In one embodiment of the methods described herein, bevacizumab is administered in a dose of about 1 to about 45 mg/kg, about 1 to about 40 mg/kg, about 1 to about 35 mg/kg, about 1 to about 30 mg/kg, about 1 to about 25 mg/kg, about 1 to about 20 mg/kg, about 1 to about 15 mg/kg, about 1 to about 10 mg/kg, about 1 to about 5 mg/kg, or about 5 to about 15 mg/kg administered daily, weekly, every two weeks, every three weeks, or every four weeks, for example. In one such embodiment, bevacizumab is administered in a dose of about 5 mg/kg to about 15 mg/kg every 2 or every 3 weeks. In another such embodiment, bevacizumab is administered in a dose of about 10 mg/kg to about 20 mg/kg every 2 or every 3 weeks.

In one embodiment of the methods described herein, bevacizumab is administered in a dose of about 15 mg/kg every 3 weeks (Q3W). In another embodiment, bevacizumab is administered in a dose of about 10 mg/kg every 2 weeks (Q2W).

Also provided herein is a method of treating NSCLC comprising a KRas$^{G12C}$ mutation in a patient having such a cancer, where the method comprises administering to the patient an effective amount of a combination therapy as described herein comprising a dosing regimen comprising: (i) administering an effective amount of Compound 1 or a pharmaceutically acceptable salt thereof at an amount of about 50 mg-500 mg QD on days 1-21 of a first 21-day cycle; and (ii) administering an effective amount of bevacizumab Q3W at an amount of 15 mg/kg on day 1 of the first 21-day cycle. In one embodiment of the method provided herein, the method is used for treating adenocarcinoma.

Also provided herein is a method of treating CRC comprising a KRas$^{G12C}$ mutation in a patient having such a cancer, where the method comprises administering to the patient an effective amount of a combination therapy as described herein comprising a dosing regimen comprising: (i) administering an effective amount of Compound 1 or a pharmaceutically acceptable salt thereof at an amount of about 50 mg-500 mg QD on days 1-21 of a first 21-day cycle; and (ii) administering an effective amount of bevacizumab Q3W at an amount of 15 mg/kg on day 1 of the first 21-day cycle.

Also provided herein is a method of treating pancreatic cancer comprising a KRas$^{G12C}$ mutation in a patient having such a cancer, where the method comprises administering to the patient an effective amount of a combination therapy as described herein comprising a dosing regimen comprising: (i) administering an effective amount of Compound 1 or a pharmaceutically acceptable salt thereof at an amount of about 50 mg-500 mg QD on days 1-21 of a first 21-day cycle; and (ii) administering an effective amount of bevacizumab Q3W at an amount of 15 mg/kg on day 1 of the first 21-day cycle.

Also provided herein is a method of treating hepatocellular carcinoma, breast cancer, renal cell carcinoma, endometrial cancer, or ovarian cancer comprising a KRas$^{G12C}$ mutation in a patient having such a cancer, where the method comprises administering to the patient an effective amount of a combination therapy as described herein comprising a dosing regimen comprising: (i) administering an effective amount of Compound 1 or a pharmaceutically acceptable salt thereof at an amount of about 50 mg-500 mg QD on days 1-21 of a first 21-day cycle; and (ii) administering an effective amount of bevacizumab Q3W at an amount of 15 mg/kg on day 1 of the first 21-day cycle.

The methods provided herein can include administration of a combination therapy described herein as part of a dosing regimen. In such one embodiment, the dosing regimen comprises one or more cycles. In another embodiment, the dosing regimen comprises at least 2 cycles. In another aspect provided herein is the dosing regimen comprises 2, 3, 4, 5, 6, 8, 10, 12, 16, 18, 20, 24, 30, 36, 42, 48, 54, 60, 66, or 72 cycles. In still another embodiment, dosing regimen comprises about 2-72, 2-66, 2-60, 2-54, 2-48, 2-42, 2-36, 2-30, 2-24, 2-18, 2-12, or 2-6 cycles. In one embodiment, the dosing regimen includes administration of a combination therapy as described herein in any number of cycles until the desired response (e.g. PFS, OS, ORR, and/or DOR) reaches a desired outcome (e.g. increase in PFS, OS, ORR, and/or DOR compared to a control described herein). In another embodiment, the dosing regimen includes administration of a combination therapy as described herein in any number of cycles until toxicity develops or the patient otherwise experiences one or more adverse events (AEs) that prevents further administration. In still another embodiment, the dosing regimen includes administration of a combination therapy as described herein in any number of cycles until disease progression.

In one embodiment of the methods described herein, a patient is administered a total of 1 to 50 doses of bevacizumab, e.g., 1 to 50 doses, 1 to 45 doses, 1 to 40 doses, 1 to 35 doses, 1 to 30 doses, 1 to 25 doses, 1 to 20 doses, 1 to 15 doses, 1 to 10 doses, 1 to 5 doses, 2 to 50 doses, 2 to 45 doses, 2 to 40 doses, 2 to 35 doses, 2 to 30 doses, 2 to 25 doses, 2 to 20 doses, 2 to 15 doses, 2 to 10 doses, 2 to 5 doses, 3 to 50 doses, 3 to 45 doses, 3 to 40 doses, 3 to 35 doses, 3 to 30 doses, 3 to 25 doses, 3 to 20 doses, 3 to 15 doses, 3 to 10 doses, 3 to 5 doses, 4 to 50 doses, 4 to 45 doses, 4 to 40 doses, 4 to 35 doses, 4 to 30 doses, 4 to 25 doses, 4 to 20 doses, 4 to 15 doses, 4 to 10 doses, 4 to 5 doses, 5 to 50 doses, 5 to 45 doses, 5 to 40 doses, 5 to 35 doses, 5 to 30 doses, 5 to 25 doses, 5 to 20 doses, 5 to 15 doses, 5 to 10 doses, 10 to 50 doses, 10 to 45 doses, 10 to 40 doses, 10 to 35 doses, 10 to 30 doses, 10 to 25 doses, 10 to 20 doses, 10 to 15 doses, 15 to 50 doses, 15 to 45 doses, 15 to 40 doses, 15 to 35 doses, 15 to 30 doses, 15 to 25 doses, 15 to 20 doses, 20 to 50 doses, 20 to 45 doses, 20 to 40 doses, 20 to 35 doses, 20 to 30 doses, 20 to 25 doses, 25 to 50 doses, 25 to 45 doses, 25 to 40 doses, 25 to 35 doses, 25 to 30 doses, 30 to 50 doses, 30 to 45 doses, 30 to 40 doses, 30 to 35 doses, 35 to 50 doses, 35 to 45 doses, 35 to 40 doses, 40 to 50 doses, 40 to 45 doses, or 45 to 50 doses. In one preferred embodiment, the doses are administered intravenously.

In certain embodiments, the therapeutic agents of the combination therapies described herein (e.g. Compound 1 or a pharmaceutically acceptable salt thereof and bevacizumab) may be administered in any suitable manner known in the art. For example, bevacizumab may be administered sequentially (on different days) or concurrently (on the same day or during the same treatment cycle) as Compound 1 or a pharmaceutically acceptable salt thereof. In one embodiment, bevacizumab is administered after administration of Compound 1 or a pharmaceutically acceptable salt thereof. In some instances, bevacizumab is administered after administration of Compound 1 or a pharmaceutically acceptable salt thereof may be administered on the same day. In one embodiment, bevacizumab may be administered after administration of Compound 1 or a pharmaceutically acceptable salt thereof on the same day. For example, Compound 1 or a pharmaceutically acceptable salt thereof can be administered on Day 1 of each cycle prior to administration of bevacizumab on Day 1 of each cycle, where Compound 1 or a pharmaceutically acceptable salt thereof is then administered QD for the next 20 days of the 21-day cycle.

In a preferred embodiment, bevacizumab is administered intravenously after Compound 1 or a pharmaceutically acceptable salt thereof (e.g. about 60 minutes). In one example, bevacizumab may be administered intravenously over 90 minutes±15 minutes. If the first infusion is tolerated, the second administration of bevacizumab is administered IV over 60 minutes±10 min. If the 60 minute administration is tolerated then all subsequent infusions may be delivered over 30 minutes±10 minutes. In some examples, the bevacizumab is administered as an intravenous push or bolus.

Also provided herein are methods for treating lung cancer comprising a KRas$^{G12C}$ mutation in a patient having such a cancer, where the method comprises administering to the patient a treatment regimen comprising an effective amount of Compound 1 or a pharmaceutically acceptable salt thereof (e.g. adipate salt) and an anti-VEGF antibody described herein (e.g., bevacizumab). In one embodiment of such methods, Compound 1 is an adipate salt and the anti-VEGF antibody described herein is bevacizumab. In another embodiment of such methods, Compound 1 or a pharmaceutically acceptable salt thereof is administered QD as described herein and in an amount as described herein (e.g. 50 mg-500 mg). In another embodiment of such methods, bevacizumab is administered Q3W as described herein and in an amount as described herein (e.g. 5-20 mg/kg). In such methods, Compound 1 or a pharmaceutically acceptable salt thereof and bevacizumab can be administered as described herein. In such methods, the lung cancer can be NSCLC comprising a KRas$^{G12C}$ mutation.

Also provided herein are methods for treating CRC comprising a KRas$^{G12C}$ mutation in a patient having such a cancer, where the method comprises administering to the patient a treatment regimen comprising an effective amount of Compound 1 or a pharmaceutically acceptable salt thereof (e.g. adipate salt) and an anti-VEGF antibody described herein (e.g., bevacizumab). In one embodiment of such methods, Compound 1 is an adipate salt and the anti-VEGF antibody described herein is bevacizumab. In another embodiment of such methods, Compound 1 or a pharmaceutically acceptable salt thereof is administered QD as described herein and in an amount as described herein (e.g. 50 mg-500 mg). In another embodiment of such methods, bevacizumab is administered Q3W as described herein and in an amount as described herein (e.g. 5-20 mg/kg). In such methods, Compound 1 or a pharmaceutically acceptable salt thereof and bevacizumab can be administered as described herein.

Also provided herein are methods for treating pancreatic cancer comprising a KRas$^{G12C}$ mutation in a patient having such a cancer, where the method comprises administering to the patient a treatment regimen comprising an effective amount of Compound 1 or a pharmaceutically acceptable salt thereof (e.g. adipate salt) and an anti-VEGF antibody described herein (e.g., bevacizumab). In one embodiment of such methods, Compound 1 is an adipate salt and the anti-VEGF antibody described herein is bevacizumab. In another embodiment of such methods, Compound 1 or a pharmaceutically acceptable salt thereof is administered QD as described herein and in an amount as described herein (e.g. 50 mg-500 mg). In another embodiment of such methods, bevacizumab is administered Q3W as described herein and in an amount as described herein (e.g. 5-20 mg/kg). In such methods, Compound 1 or a pharmaceutically acceptable salt thereof and bevacizumab can be administered as described herein.

Also provided herein are methods for treating hepatocellular carcinoma, breast cancer, renal cell carcinoma, endometrial cancer, or ovarian cancer comprising a KRas$^{G12C}$ mutation in a patient having such a cancer, where the method comprises administering to the patient a treatment regimen comprising an effective amount of Compound 1 or a pharmaceutically acceptable salt thereof (e.g. adipate salt) and an anti-VEGF antibody described herein (e.g., bevacizumab). In one embodiment of such methods, Compound 1 is an adipate salt and the anti-VEGF antibody described herein is bevacizumab. In another embodiment of such methods, Compound 1 or a pharmaceutically acceptable salt thereof is administered QD as described herein and in an amount as described herein (e.g. 50 mg-500 mg). In another embodiment of such methods, bevacizumab is administered Q3W as described herein and in an amount as described herein (e.g. 5-20 mg/kg). In such methods, Compound 1 or a pharmaceutically acceptable salt thereof and bevacizumab can be administered as described herein.

In some instances, the treatment regimen includes administration of one or more additional therapies where the additional therapy is one or more side-effect limiting agents (e.g., agents intended to lessen the occurrence and/or severity of side effects of treatment, such as anti-nausea agents, a corticosteroid (e.g., prednisone or an equivalent, e.g., at a dose of 1-2 mg/kg/day), hormone replacement medicine(s), and the like).

A patient as provided herein, must be evaluated and have a confirmed test result for a KRas$^{G12C}$ mutation as set forth herein. A patient described herein having diagnosed NSCLC must not have a known concomitant second oncogenic driver (e.g., for NSCLC: sensitizing EGFR mutations, ALK rearrangement, ROS1 rearrangement, BRAF V600E mutation, NTRK fusions, RET fusions; or for adenocarcinoma of the colon or rectum: BRAF V600E mutation, ERBB2 amplification). In one embodiment, such second oncogenic drivers are determined using NGS (e.g. by the Foundation Medicine, Inc. (FMI) NGS assay).

In one embodiment, a patient described herein does not have known and untreated, or active central nervous system (CNS) metastases (progressing or requiring anticonvulsants or corticosteroids for symptomatic control). A patient may be treated using the methods described herein where such patients have a history of treated CNS metastases where such a patient has: (1) measurable or evaluable disease outside the CNS; (2) no history of intracranial hemorrhage or spinal cord hemorrhage; (3) no ongoing requirement for corticosteroids as therapy for CNS metastases, with corticosteroids discontinued for ≥2 weeks prior to administration of a combination therapy as described herein and no ongoing symptoms attributed to CNS metastases; (4) no stereotactic radiation within 7 days or whole-brain radiation within 14 days prior to Day 1 of Cycle 1 as described herein; and (5) no evidence of interim progression between the completion of CNS-directed therapy and the screening radiographic study.

In one embodiment, a patient described herein has received prior treatment with a KRas$^{G12C}$ specific inhibitor.

In another embodiment, a patient described herein has not received treatment with chemotherapy, immunotherapy, or biologic therapy as anti-cancer therapy within 3 weeks prior to administration of a combination therapy described herein, or endocrine therapy within 2 weeks prior to administration of a combination therapy described herein, except for the following:
 (a) hormonal therapy with gonadotropin-releasing hormone (GnRH) agonists or antagonists for endocrine sensitive cancers (e.g., prostate, endometrial, hormone receptor-positive breast cancer);
 (b) kinase inhibitors, approved by regulatory authorities, may be used up to 2 weeks prior to administration of a combination therapy described herein, provided any drug-related toxicity has completely resolved; or
 (c) treatment with an investigational agent within 3 weeks or five half-lives prior to administration of a combination therapy described herein, whichever is shorter.

In another embodiment, a patient described herein has not received radiation therapy (other than palliative radiation to bony metastases and radiation to CNS metastases as described above) as cancer therapy within 4 weeks prior to initiation of administration of a combination therapy described herein. In still another embodiment, a patient described herein has not received palliative radiation to bony metastases within 2 weeks prior to administration of a combination therapy described herein.

In another embodiment, a patient described herein does not have poorly controlled hypertension (e.g., systolic>150 mmHg or diastolic>100 mmHg). In another embodiment, a patient described herein does not have a history or evidence of inherited bleeding diathesis or coagulopathy with the risk of bleeding. In another embodiment, a patient described herein does not have current or recent (e.g. <10 days prior to initiation of study treatment) use of aspirin (>325 mg/day), or clopidogrel (>75 mg/day). In still another embodiment, a patient described herein does not have a history of thrombotic disorders within the last 6 months prior to initiation of study treatment. In another embodiment, a patient described herein does not have ≥2+ proteinuria on dipstick urinalysis during screening or at planned Cycle 1 Day 1 assessment should undergo a 24-hour urine collection and must demonstrate ≤1 g of protein in 24 hours prior to administration of an anti-VEGF antibody (e.g. bevacizumab) as described herein.

In one embodiment, a patient described herein does not have a serious, non-healing wound, active ulcer, or untreated bone fracture. In another embodiment, a patient described herein does not have a history of abdominal fistula, gastrointestinal perforation or intra-abdominal abscess within 6 months of administration of an anti-VEGF antibody e.g. bevacizumab) as described herein. In another embodiment, a patient described herein does not have pulmonary hemorrhage/hemoptysis (>½ teaspoon red blood) within one month prior to administration of an anti-VEGF antibody e.g. bevacizumab) as described herein. In still another embodiment, a patient described herein does not have clear tumor infiltration into the thoracic great vessels seen on imaging or clear cavitation of pulmonary lesions seen on imaging.

Further provided herein is the use (UL1) of a combination therapy described herein comprising Compound 1 or a pharmaceutically acceptable salt thereof and bevacizumab for the treatment of lung cancer as described herein. In one embodiment, is a use (UL2) of a combination therapy described herein comprising Compound 1 or a pharmaceutically acceptable salt thereof and bevacizumab for the treatment of NSCLC as described herein.

Further provided herein is the use (UL3) of a combination therapy described herein comprising Compound 1 or a pharmaceutically acceptable salt thereof and bevacizumab for the treatment of lung cancer as described herein comprising a dosing regimen comprising: (i) administering Compound 1 or a pharmaceutically acceptable salt thereof QD on days 1-21 of a first 21-day cycle; and (ii) administering bevacizumab Q3W on day 1 of the first 21-day cycle. In one such embodiment, Compound 1 or a pharmaceutically acceptable salt thereof is administered at an amount of about 50-500 mg. In another such embodiment, bevacizumab is administered at an amount of about 5-20 mg/kg.

Further provided herein is the use (UL4) of a combination therapy described herein comprising Compound 1 or a pharmaceutically acceptable salt thereof and bevacizumab for the treatment of lung cancer as described herein comprising a dosing regimen comprising: (i) administering about 50-500 mg Compound 1 or a pharmaceutically acceptable salt thereof QD on days 1-21 of a first 21-day cycle; and (ii) administering about 15 mg/kg bevacizumab Q3W on day 1 of the first 21-day cycle. In one such embodiment, the dosing regimen includes 2 or more cycles as described herein.

Further provided herein is the use (UL5) of a combination therapy described herein comprising Compound 1 or a pharmaceutically acceptable salt thereof and bevacizumab for the manufacture of a medicament for the treatment of lung cancer as described herein.

Further provided herein is the use (UL6) of a combination therapy described herein comprising Compound 1 or a pharmaceutically acceptable salt thereof and bevacizumab for the manufacture of a medicament for the treatment of lung cancer as described herein comprising a dosing regimen comprising: (i) administering Compound 1 or a pharmaceutically acceptable salt thereof QD on days 1-21 of a first 21-day cycle; and (ii) administering bevacizumab Q3W on day 1 of the first 21-day cycle. In one such embodiment, Compound 1 or a pharmaceutically acceptable salt thereof is administered at an amount of about 50-500 mg. In another such embodiment, bevacizumab is administered at an amount of about 5-20 mg/kg.

Further provided herein is the use (UL7) of a combination therapy described herein comprising Compound 1 or a pharmaceutically acceptable salt thereof and bevacizumab for the manufacture of a medicament for the treatment of lung cancer as described herein comprising a dosing regimen comprising: (i) administering about 50-500 mg Compound 1 or a pharmaceutically acceptable salt thereof QD on days 1-21 of a first 21-day cycle; and (ii) administering about 15 mg/kg bevacizumab Q3W on day 1 of the first 21-day cycle. In one such embodiment, the dosing regimen includes 2 or more cycles as described herein.

In such embodiments of the uses described herein, the lung cancer can be NSCLC. In another such embodiment of the uses described herein, a patient described herein is diagnosed with NSCLC mediated by a $KRas^{G12C}$ mutation.

Further provided herein is the use (UC1) of a combination therapy described herein comprising Compound 1 or a pharmaceutically acceptable salt thereof and bevacizumab for the treatment of CRC as described herein.

Further provided herein is the use (UC2) of a combination therapy described herein comprising Compound 1 or a pharmaceutically acceptable salt thereof and bevacizumab for the treatment of CRC as described herein comprising a dosing regimen comprising: (i) administering Compound 1 or a pharmaceutically acceptable salt thereof QD on days 1-21 of a first 21-day cycle; and (ii) administering bevacizumab Q3W on day 1 of the first 21-day cycle. In one such embodiment, Compound 1 or a pharmaceutically acceptable salt thereof is administered at an amount of about 50-500 mg. In another such embodiment, bevacizumab is administered at an amount of about 5-20 mg/kg.

Further provided herein is the use (UC3) of a combination therapy described herein comprising Compound 1 or a pharmaceutically acceptable salt thereof and bevacizumab for the treatment of CRC as described herein comprising a dosing regimen comprising: (i) administering about 50-500 mg Compound 1 or a pharmaceutically acceptable salt thereof QD on days 1-21 of a first 21-day cycle; and (ii) administering about 15 mg/kg bevacizumab Q3W on day 1 of the first 21-day cycle. In one such embodiment, the dosing regimen includes 2 or more cycles as described herein.

Further provided herein is the use (UC4) of a combination therapy described herein comprising Compound 1 or a pharmaceutically acceptable salt thereof and bevacizumab for the manufacture of a medicament for the treatment of CRC as described herein.

Further provided herein is the use (UC5) of a combination therapy described herein comprising Compound 1 or a pharmaceutically acceptable salt thereof and bevacizumab for the manufacture of a medicament for the treatment of CRC as described herein comprising a dosing regimen comprising: (i) administering Compound 1 or a pharmaceutically acceptable salt thereof QD on days 1-21 of a first 21-day cycle; and (ii) administering bevacizumab Q3W on day 1 of the first 21-day cycle. In one such embodiment, Compound 1 or a pharmaceutically acceptable salt thereof is administered at an amount of about 50-500 mg. In another such embodiment, bevacizumab is administered at an amount of about 5-20 mg/kg.

Further provided herein is the use (UC6) of a combination therapy described herein comprising Compound 1 or a pharmaceutically acceptable salt thereof and bevacizumab for the manufacture of a medicament for the treatment of CRC as described herein comprising a dosing regimen comprising: (i) administering about 50-500 mg Compound 1 or a pharmaceutically acceptable salt thereof QD on days 1-21 of a first 21-day cycle; and (ii) administering about 15 mg/kg bevacizumab Q3W on day 1 of the first 21-day cycle. In one such embodiment, the dosing regimen includes 2 or more cycles as described herein.

Further provided herein is the use (UP1) of a combination therapy described herein comprising Compound 1 or a pharmaceutically acceptable salt thereof and bevacizumab for the treatment of pancreatic cancer as described herein.

Further provided herein is the use (UP2) of a combination therapy described herein comprising Compound 1 or a pharmaceutically acceptable salt thereof and bevacizumab for the treatment of pancreatic cancer as described herein comprising a dosing regimen comprising: (i) administering Compound 1 or a pharmaceutically acceptable salt thereof QD on days 1-21 of a first 21-day cycle; and (ii) administering bevacizumab Q3W on day 1 of the first 21-day cycle. In one such embodiment, Compound 1 or a pharmaceutically acceptable salt thereof is administered at an amount of about 50-500 mg. In another such embodiment, bevacizumab is administered at an amount of about 5-20 mg/kg.

Further provided herein is the use (UP3) of a combination therapy described herein comprising Compound 1 or a pharmaceutically acceptable salt thereof and bevacizumab for the treatment of pancreatic cancer as described herein comprising a dosing regimen comprising: (i) administering about 50-500 mg Compound 1 or a pharmaceutically acceptable salt thereof QD on days 1-21 of a first 21-day cycle; and (ii) administering about 15 mg/kg bevacizumab Q3W on day 1 of the first 21-day cycle. In one such embodiment, the dosing regimen includes 2 or more cycles as described herein.

Further provided herein is the use (UP4) of a combination therapy described herein comprising Compound 1 or a pharmaceutically acceptable salt thereof and bevacizumab for the manufacture of a medicament for the treatment of pancreatic cancer as described herein.

Further provided herein is the use (UP5) of a combination therapy described herein comprising Compound 1 or a pharmaceutically acceptable salt thereof and bevacizumab for the manufacture of a medicament for the treatment of pancreatic cancer as described herein comprising a dosing regimen comprising: (i) administering Compound 1 or a pharmaceutically acceptable salt thereof QD on days 1-21 of a first 21-day cycle; and (ii) administering bevacizumab Q3W on day 1 of the first 21-day cycle. In one such embodiment, Compound 1 or a pharmaceutically acceptable salt thereof is administered at an amount of about 50-500 mg. In another such embodiment, bevacizumab is administered at an amount of about 5-20 mg/kg.

Further provided herein is the use (UP6) of a combination therapy described herein comprising Compound 1 or a pharmaceutically acceptable salt thereof and bevacizumab for the manufacture of a medicament for the treatment of pancreatic cancer as described herein comprising a dosing regimen comprising: (i) administering about 50-500 mg Compound 1 or a pharmaceutically acceptable salt thereof QD on days 1-21 of a first 21-day cycle; and (ii) administering about 15 mg/kg bevacizumab Q3W on day 1 of the first 21-day cycle. In one such embodiment, the dosing regimen includes 2 or more cycles as described herein.

Further provided herein is the use (UA1) of a combination therapy described herein comprising Compound 1 or a pharmaceutically acceptable salt thereof and bevacizumab for the treatment of hepatocellular carcinoma, breast cancer, renal cell carcinoma, endometrial cancer, or ovarian cancer as described herein.

Further provided herein is the use (UA2) of a combination therapy described herein comprising Compound 1 or a pharmaceutically acceptable salt thereof and bevacizumab for the treatment of hepatocellular carcinoma, breast cancer, renal cell carcinoma, endometrial cancer, or ovarian cancer as described herein comprising a dosing regimen comprising: (i) administering Compound 1 or a pharmaceutically acceptable salt thereof QD on days 1-21 of a first 21-day cycle; and (ii) administering bevacizumab Q3W on day 1 of the first 21-day cycle. In one such embodiment, Compound 1 or a pharmaceutically acceptable salt thereof is administered at an amount of about 50-500 mg. In another such embodiment, bevacizumab is administered at an amount of about 5-20 mg/kg.

Further provided herein is the use (UA3) of a combination therapy described herein comprising Compound 1 or a pharmaceutically acceptable salt thereof and bevacizumab for the treatment of hepatocellular carcinoma, breast cancer, renal cell carcinoma, endometrial cancer, or ovarian cancer as described herein comprising a dosing regimen comprising: (i) administering about 50-500 mg Compound 1 or a pharmaceutically acceptable salt thereof QD on days 1-21 of a first 21-day cycle; and (ii) administering about 15 mg/kg bevacizumab Q3W on day 1 of the first 21-day cycle. In one such embodiment, the dosing regimen includes 2 or more cycles as described herein.

Further provided herein is the use (UA4) of a combination therapy described herein comprising Compound 1 or a pharmaceutically acceptable salt thereof and bevacizumab for the manufacture of a medicament for the treatment of hepatocellular carcinoma, breast cancer, renal cell carcinoma, endometrial cancer, or ovarian cancer as described herein.

Further provided herein is the use (UA5) of a combination therapy described herein comprising Compound 1 or a pharmaceutically acceptable salt thereof and bevacizumab for the manufacture of a medicament for the treatment of hepatocellular carcinoma, breast cancer, renal cell carcinoma, endometrial cancer, or ovarian cancer as described herein comprising a dosing regimen comprising: (i) administering Compound 1 or a pharmaceutically acceptable salt thereof QD on days 1-21 of a first 21-day cycle; and (ii) administering bevacizumab Q3W on day 1 of the first 21-day cycle. In one such embodiment, Compound 1 or a pharmaceutically acceptable salt thereof is administered at an amount of about 50-500 mg. In another such embodiment, bevacizumab is administered at an amount of about 5-20 mg/kg.

Further provided herein is the use (UA6) of a combination therapy described herein comprising Compound 1 or a pharmaceutically acceptable salt thereof and bevacizumab for the manufacture of a medicament for the treatment of hepatocellular carcinoma, breast cancer, renal cell carcinoma, endometrial cancer, or ovarian cancer as described herein comprising a dosing regimen comprising: (i) administering about 50-500 mg Compound 1 or a pharmaceutically acceptable salt thereof QD on days 1-21 of a first 21-day cycle; and (ii) administering about 15 mg/kg bevacizumab Q3W on day 1 of the first 21-day cycle. In one such embodiment, the dosing regimen includes 2 or more cycles as described herein.

The development of combination treatments poses challenges including, for example, the selection of agents for combination therapy that may lead to improved efficacy while maintaining acceptable toxicity. One particular challenge is the need to distinguish the incremental toxicity of the combination. In one embodiment of the methods described herein the combination therapy described herein (e.g. Compound 1 or a pharmaceutically acceptable salt thereof and bevacizumab) is administered in a dosing regimen comprising a staggered dosing schedule. In one such embodiment, the patient has a reduced number or grade of adverse events (AEs) comparable to a control (e.g. SOC therapy, treatment with one agent described herein (e.g. Compound 1 or a pharmaceutically acceptable salt thereof or bevacizumab) alone).

It is generally understood that the when an adverse event occurs, four options exist: (1) continue treatment as-is with optional concomitant therapy; (2) adjust the dose of one or more agents in the dosing regimen; (3) suspend administration of one or more agents in the dosing regimen; or (4) discontinue administration of one or more agents in the dosing regimen. In one embodiment, the amount of Compound 1 or a pharmaceutically acceptable salt thereof is not modified. In another embodiment, the amount of bevacizumab administered is not modified. In one embodiment, where the administration of bevacizumab is interrupted, the next administration of Compound 1 or a pharmaceutically acceptable salt thereof occurs on the same day as administration of bevacizumab is resumed. In one embodiment, Compound 1 or a pharmaceutically acceptable salt thereof is administered without food (i.e. a patient should not eat at least 2 hours before and 1 hour after administration).

In one embodiment, a patient described herein experiences gastrointestinal toxicity as an AE at a grade of less than or equal to 2. In one such embodiment, the gastrointestinal toxicity is diarrhea, nausea, or vomiting. In another embodiment, a patient described herein experiences phototoxicity. In such embodiments, the patient should wear sunscreen and protective clothing outdoors.

Patients described herein can also be administered concomitant therapies including: (a) anti-seizure medications or warfarin; (b) oral contraceptives or other allowed maintenance therapy; (c) anti-emetics and anti-diarrheal medications provided that such medications should not be administered prophylactically before initial treatment with study drug; (d) pain medications administered per standard clinical practice; (e) bisphosphonate and denosumab therapy for bone metastases or osteopenia/osteoporosis; or (f) multivitamins, calcium, and vitamins C, D, and E supplements.

Patients described herein may not concomitantly take therapies including (1) Strong/moderate CYP3A4 inhibitors (e.g. atazanavir, ritonavir, indinavir, nelfinavir, saquinavir, clarithromycin, telithromycin, erythromycin, troleandomycin, fluconazole, itraconazole, ketoconazole, voriconazole, posaconazole, aprepitant, conivaptan, fluvoxamine, diltiazem, nefazodone, mibefradil, verapamil, and grapefruit juice or grapefruit supplements) or (2) Strong/moderate CYP3A4 inducers (e.g. rifampin, carbamazepine, phenytoin, oxcarbazepine, phenobarbital, efavirenz, nevirapine, etravirine, modafinil, hyperforin (St. John's Wort), and cyproterone).

In another embodiment, patients described herein are not administered any of the following therapies:
  (a) Any other investigational therapy (excluding Compound 1 or a pharmaceutically acceptable salt thereof or bevacizumab) within 3 weeks or five half-lives prior to administration of a combination therapy described herein, whichever is shorter, or during such treatment;
  (b) Concomitant therapy intended for the treatment of cancer whether approved by the FDA or experimental, including chemotherapy, radiotherapy, immunotherapy, biologic therapy, herbal therapy, or hormonal therapy except for the following:
    (i) Hormonal therapy with gonadotropin-releasing hormone (GnRH) agonists or antagonists for endocrine sensitive cancers (e.g., prostate, endometrial, hormone receptor-positive breast cancer);

(ii) Hormone replacement therapy or oral contraception;
(c) Radiotherapy for unequivocal progressive disease with the exception of new brain metastases in the setting of systemic response as follows: patients who have demonstrated control of their systemic disease (defined as having received clinical benefit [i.e., a PR, CR, or SD for ≥3 months]), but who have developed brain metastases that are treatable with radiation, will be allowed to continue to receive therapy with Compound 1 or a pharmaceutically acceptable salt thereof during the study until they either experience systemic progression of their disease and/or further progression in the brain (based on investigator assessments).
(d) Quinidine or other anti-arrhythmic agents; or
(e) Initiation or increased dose of hematopoietic colony-stimulating factors (CSFs; e.g., granulocyte CSF; filgrastim, granulocyte/macrophage CSF; sargramostim, pegfilgrastim, erythropoietin, darbepoetin, and thrombopoietin) from 7 days before Cycle 1, Day 1;

In one embodiment of such methods, the patient is diagnosed with a cancer described herein. In another embodiment of such methods, the sample is a tumor sample taken from the subject. In one such embodiment, the sample is taken before administration of any therapy described herein. In another such embodiment, the sample is taken before administration of at least one agent described herein. In some embodiments, tumor samples can be taken at specified intervals during treatment with a combination therapy described herein to assess treatment.

Determining whether a tumor or cancer comprises a $KRas^{G12C}$ mutation can be undertaken by assessing the nucleotide sequence encoding the K-Ras protein, by assessing the amino acid sequence of the K-Ras protein, or by assessing the characteristics of a putative K-Ras mutant protein. The sequence of wild-type human K-Ras (e.g. Accession No. NP203524) is known in the art. In one such embodiment, a sample from a patient described herein is assessed for a $KRas^{G12C}$ mutation using, for example, immunohistochemistry (IHC) or NGS sequencing.

Further provided herein are methods of treating tumor agnostic cancer comprising a $KRas^{G12C}$ mutation by administering a combination therapy as described herein. In one embodiment of such methods, the method comprises:
(a) determining the absence or presence of a $KRas^{G12C}$ mutation in a sample taken from a patient with a suspected diagnosed cancer; and
(b) administering to the patient a combination therapy as described herein comprising an effective amount of Compound 1 or a pharmaceutically acceptable salt thereof and bevacizumab.

In one such embodiment, Compound 1 or a pharmaceutically acceptable salt thereof is administered QD at an amount of about 50-500 mg. In another such embodiment, bevacizumab is administered Q3W at an amount of about 5-20 mg/kg.

Further provided herein are methods of treating tumor agnostic cancer comprising a $KRas^{G12C}$ mutation where the method comprises:
(a) determining the absence or presence of a $KRas^{G12C}$ mutation in a sample taken from a patient with a suspected diagnosed cancer; and
(b) administering to the patient a combination therapy as described herein comprising dosing regimen comprising: (i) administering 50 mg-500 mg Compound 1 or a pharmaceutically acceptable salt thereof QD on days 1-21 of a first 21-day cycle; and (ii) administering 15 mg/kg bevacizumab Q3W on day 1 of the first 21-day cycle.

In one embodiment of the methods provided herein a patient is diagnosed having a CR following treatment with a combination therapy according to the methods provided herein. In one embodiment of the methods provided herein a patient is diagnosed having a PR following treatment with a combination therapy according to the methods provided herein. In one embodiment of the methods provided herein a patient is diagnosed having SD following treatment with a combination therapy according to the methods provided herein.

Also provided herein are methods of inhibiting tumor growth or producing tumor regression in a patient described herein by administering a combination therapy described herein. In one embodiment provided herein is a method of inhibiting tumor growth in a patient having a cancer described herein by administering a combination therapy comprising Compound 1 or a pharmaceutically acceptable salt thereof and bevacizumab in one or more 21-day cycles as described herein. In one embodiment provided herein is a method of inhibiting tumor growth in a patient having NSCLC, CRC, or pancreatic cancer as described herein by administering a combination therapy comprising Compound 1 or a pharmaceutically acceptable salt thereof and bevacizumab in one or more 21-day cycles as described herein.

In one embodiment provided herein is a method of producing or improving tumor regression in a patient having a cancer described herein by administering a combination therapy comprising administering Compound 1 or a pharmaceutically acceptable salt thereof and bevacizumab in one or more 21-day cycles as described herein. In one embodiment provided herein is a method of producing or improving tumor regression in a patient having NSCLC, CRC, or pancreatic cancer described herein by administering a combination therapy comprising administering Compound 1 or a pharmaceutically acceptable salt thereof and bevacizumab in one or more 21-day cycles as described herein.

Kits

The combination therapies described herein can be provided as a kit comprising one or more of the agents described herein for administration. In one embodiment, the kit includes Compound 1 or a pharmaceutically acceptable salt thereof (e.g. Compound 1 adipate) for administration in combination with bevacizumab as described herein. In another embodiment, the kit includes Compound 1 or a pharmaceutically acceptable salt thereof (e.g. Compound 1 adipate) packaged together with bevacizumab, where the kit comprises separate formulated dosages of each agent.

Also provided herein is an article of manufacture or a kit comprising Compound 1 or a pharmaceutically acceptable salt thereof (e.g. Compound 1 adipate) and an anti-VEGF antibody (e.g., bevacizumab). In some instances, the article of manufacture further comprises package insert comprising instructions for using the anti-VEGF antibody to treat or delay progression of a solid tumor (e.g. lung cancer, CRC, or pancreatic cancer as described herein). In one such embodiment, the cancer is NSCLC. In one embodiment, the article of manufacture further comprises package insert comprising instructions for using bevacizumab in combination with Compound 1 or a pharmaceutically acceptable salt thereof (e.g. Compound 1 adipate) to treat or delay progression of NSCLC in a patient.

In some instances, the anti-VEGF antibody (e.g., bevacizumab) and Compound 1 or a pharmaceutically acceptable salt thereof (e.g. Compound 1 adipate) are in the same container or separate containers. Suitable containers include, for example, bottles, vials, bags and syringes. The container may be formed from a variety of materials such as glass, plastic (such as polyvinyl chloride or polyolefin), or metal alloy (such as stainless steel or hastelloy). In some instances, the container holds the formulation and the label on, or associated with, the container may indicate directions for use. The article of manufacture or kit may further include other materials desirable from a commercial and user standpoint, including other buffers, diluents, filters, needles, syringes, and package inserts with instructions for use. In some instances, the article of manufacture further includes one or more of another agent (e.g., an additional chemotherapeutic agent or anti-neoplastic agent). Suitable containers for the one or more agents include, for example, bottles, vials, bags and syringes.

Any of the articles of manufacture or kits described herein may include instructions to administer Compound 1 or a pharmaceutically acceptable salt thereof (e.g. Compound 1 adipate) and/or the anti-VEGF antibody (e.g., bevacizumab) to a patient in accordance with any of the methods described herein.

Biomarkers

In one embodiment, the alkylation of $KRas^{G12C}$ by Compound 1 or a pharmaceutically acceptable salt thereof is measured in the patient. In one such embodiment, the measurement is performed using a sample and tested for alkylation of $KRas^{G12C}$ as provided herein. In another embodiment, assessment of ctDNA biomarkers (e.g., $KRas^{G12C}$) from peripheral blood is performed.

In one embodiment, modulation of KRAS/MAPK target genes (e.g., DUSP6, SPRY4), pathway components (e.g., pERK, pS6), and related biomarkers (e.g., Ki67) through analysis of paired pre-treatment and on-treatment fresh tumor biopsies is performed.

Embodiments

Provided below are some exemplary embodiments of the invention.

Embodiment No. 1: A combination therapy comprising:

(a)

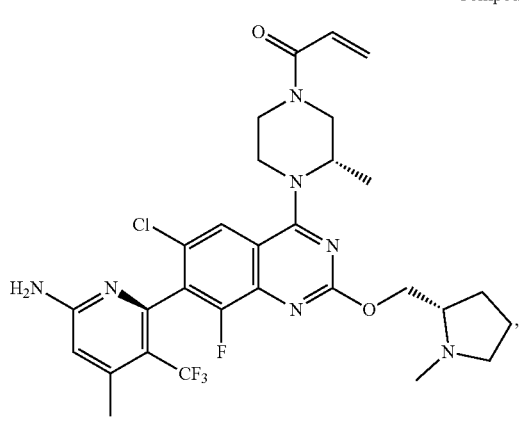

Compound 1 or a pharmaceutically acceptable salt thereof and;
(b) an anti-VEGF antibody.

Embodiment No. 2: The combination therapy of embodiment 1 or 2, wherein the anti-VEGF antibody is bevacizumab.

Embodiment No. 3: The combination therapy of any one of embodiment 1 or embodiment 2, wherein Compound 1 is an adipate salt thereof.

Embodiment No. 4: The combination of any one of embodiments 1-3, wherein Compound 1 or a pharmaceutically acceptable salt thereof is administered QD on days 1-21 of a first 21-day cycle and bevacizumab administered Q3W on day 1 of the first 21-day cycle.

Embodiment No. 5: The combination therapy of any one of embodiments 1-4, wherein Compound 1 or a pharmaceutically acceptable salt thereof is administered orally as a tablet or capsule.

Embodiment No. 6: The combination therapy of any one of embodiments 1-5, wherein Compound 1 or a pharmaceutically acceptable salt thereof is administered at an amount of about 50 mg-500 mg.

Embodiment No. 7: The combination therapy of any one of embodiments 1-6, wherein Compound 1 or a pharmaceutically acceptable salt thereof is administered at an amount of about 5 mg, 25 mg, 50 mg, 100 mg, 150 mg, 200 mg, 250 mg, 300 mg, 400 mg or 500 mg.

Embodiment No. 8: The combination therapy of any one of embodiments 2-7, wherein bevacizumab is administered at an amount of about 5-20 mg/kg Q3W.

Embodiment No. 9: The combination therapy of embodiment 5, wherein bevacizumab is administered at an amount of about 10-20 mg/kg Q3W.

Embodiment No. 10: The combination therapy of any one of embodiments 2-9, wherein bevacizumab is administered to the patient intravenously at a dose of about 15 mg/kg Q3W.

Embodiment No. 11: The combination therapy of any one of embodiment 1-10 for use in lung cancer comprising a $KRas^{G12C}$ mutation.

Embodiment No. 12: The combination therapy of embodiment 11, wherein the lung cancer is non-small cell lung carcinoma (NSCLC).

Embodiment No. 13: The combination therapy of any one of embodiment 1-10 for use in colorectal cancer (CRC) comprising a $KRas^{G12C}$ mutation.

Embodiment No. 14: The combination therapy of any one of embodiment 1-10 for use in pancreatic cancer comprising a $KRas^{G12C}$ mutation.

Embodiment No. 15: The combination therapy of any one of embodiment 1-10 for use in hepatocellular carcinoma, breast cancer, renal cell carcinoma, endometrial cancer, or ovarian cancer comprising a $KRas^{G12C}$ mutation.

Embodiment No. 16: A combination therapy comprising:
(a) Compound 1 or a pharmaceutically acceptable salt thereof administered QD on days 1-21 of a first 21-day cycle and;
(b) bevacizumab administered Q3W on day 1 of the first 21-day cycle.

Embodiment No. 17: The combination therapy of embodiment 16, wherein Compound 1 or a pharmaceutically acceptable salt thereof is administered QD at an amount of about 50 mg-500 mg on days 1-21 of a first 21-day cycle and bevacizumab is administered Q3W at an amount of about 15 mg/kg on day 1 of the first 21-day cycle.

Embodiment No. 18: A method of treating lung cancer mediated by a $KRas^{G12C}$ mutation in a patient having such a lung cancer, the method comprising administering an effective amount of a combination therapy comprising:
(a) Compound 1 or a pharmaceutically acceptable salt thereof and;
(b) an anti-VEGF antibody.

Embodiment No. 19: The combination therapy of any one of embodiment 18, wherein the lung cancer is NSCLC.

Embodiment No. 20: The combination therapy of any one of embodiment 18, wherein the lung cancer is adenocarcinoma, squamous-cell lung carcinoma or large-cell lung carcinoma.

Embodiment No. 21: A method of treating colorectal cancer (CRC) mediated by a KRas$^{G12C}$ mutation in a patient having CRC, the method comprising administering an effective amount of a combination therapy comprising:
(a) Compound 1 or a pharmaceutically acceptable salt thereof and;
(b) an anti-VEGF antibody.

Embodiment No. 22: A method of treating pancreatic cancer mediated by a KRas$^{G12C}$ mutation in a patient having such a lung cancer, the method comprising administering an effective amount of a combination therapy comprising:
(a) Compound 1 or a pharmaceutically acceptable salt thereof and;
(b) an anti-VEGF antibody.

Embodiment No. 23: A method of treating hepatocellular carcinoma, breast cancer, renal cell carcinoma, endometrial cancer, or ovarian cancer mediated by a KRas$^{G12C}$ mutation in a patient having such a cancer, the method comprising administering an effective amount of a combination therapy comprising:
(a) Compound 1 or a pharmaceutically acceptable salt thereof and;
(b) an anti-VEGF antibody.

Embodiment No. 24: The method of any one of embodiments 18-23, wherein the anti-VEGF antibody is bevacizumab.

Embodiment No. 25: The method of any one of embodiments 18-24, wherein Compound 1 is an adipate salt thereof.

Embodiment No. 26: The method of any one of embodiments 18-25, wherein Compound 1 or a pharmaceutically acceptable salt thereof is administered QD on days 1-21 of a first 21-day cycle and bevacizumab administered Q3W on day 1 of the first 21-day cycle.

Embodiment No. 27: The method of any one of embodiments 18-26, wherein Compound 1 or a pharmaceutically acceptable salt thereof is administered orally as a tablet or capsule.

Embodiment No. 28: The method of any one of embodiments 18-27, wherein Compound 1 or a pharmaceutically acceptable salt thereof is administered at an amount of about 50 mg-500 mg.

Embodiment No. 29: The method of any one of embodiments 18-28, wherein Compound 1 or a pharmaceutically acceptable salt thereof is administered at an amount of about 5 mg, 25 mg, 50 mg, 100 mg, 150 mg, 200 mg, 250 mg, 300 mg, 400 mg or 500 mg.

Embodiment No. 30: The method of any one of embodiments 18-29, wherein bevacizumab is administered Q3W at an amount of about 5-20 mg/kg.

Embodiment No. 31: The method of any one of embodiments 18-30, wherein bevacizumab is administered Q3W at an amount of about 10-20 mg/kg.

Embodiment No. 32: The method of any one of embodiments 18-31, wherein bevacizumab is administered Q3W to the patient intravenously at a dose of about 15 mg/kg.

Embodiment No. 33: A method of treating NSCLC comprising a KRas$^{G12C}$ mutation in a patient having such a cancer, the method comprising administering to the patient an effective amount of a combination therapy comprising:
(a) Compound 1 or a pharmaceutically acceptable salt thereof, wherein Compound 1 or a pharmaceutically acceptable salt thereof QD on days 1-21 of a first 21-day cycle and;
(b) bevacizumab administered Q3W on day 1 of the first 21-day cycle.

Embodiment No. 34: The method of embodiment 33, wherein:
(a) Compound 1 or a pharmaceutically acceptable salt thereof is administered at an amount of about 50 mg-500 mg QD on days 1-21 of the first 21-day cycle; and
(b) bevacizumab is administered Q3W at an amount of 5-20 mg/kg on day 1 of the first 21-day cycle.

Embodiment No. 35: The method of any one of embodiments 18-34, wherein bevacizumab is administered after administration of Compound 1 or a pharmaceutically acceptable salt thereof.

Embodiment No. 36: A method of treating NSCLC, CRC, or pancreatic cancer in a patient having such a cancer, the method comprising administering to the patient a treatment regimen comprising an effective amount of Compound 1 or a pharmaceutically acceptable salt thereof and an effective amount of an anti-VEGF antibody.

Embodiment No. 37: The method of embodiment 32, wherein Compound 1 is an adipate salt.

Embodiment No. 38: The method of embodiment 32 or embodiment 33, wherein the anti-VEGF is bevacizumab.

Embodiment No. 39: The method of any one of embodiments 36-38, wherein:
(a) Compound 1 or a pharmaceutically acceptable salt thereof is administered at an amount of about 50 mg-500 mg QD on days 1-21 of the first 21-day cycle; and
(b) bevacizumab is administered Q3W at an amount of 5-20 mg/kg on day 1 of the first 21-day cycle.

Embodiment No. 40: The method of any one of embodiments 18-39, wherein the patient is diagnosed as not having a mutation selected from the group consisting of sensitizing EGFR mutations, ALK rearrangement, ROS1 rearrangement, BRAF V600E mutation, NTRK fusions, and RET fusions, or a combination thereof.

Embodiment No. 41: Use of a combination therapy comprising Compound 1 or a pharmaceutically acceptable salt thereof and bevacizumab for the treatment of lung cancer, CRC, or pancreatic cancer as described herein.

Embodiment No. 42: The use of embodiment 41, further comprising a dosing regimen comprising: (i) administering Compound 1 or a pharmaceutically acceptable salt thereof QD on days 1-21 of a first 21-day cycle; and (ii) administering bevacizumab Q3W on day 1 of the first 21-day cycle.

Embodiment No. 43: The use of embodiment 41 or embodiment 42, further comprising (i) administering about 50-500 mg Compound 1 or a pharmaceutically acceptable salt thereof QD on days 1-21 of the first 21-day cycle; and (ii) administering about 5-20 mg/kg bevacizumab Q3W on day 1 of the first 21-day cycle.

Embodiment No. 44: Use of a combination therapy comprising Compound 1 or a pharmaceutically acceptable salt thereof and bevacizumab for the manufacture of a medicament for the treatment of lung cancer, CRC, or pancreatic cancer.

Embodiment No. 45: The use of embodiment 44, further comprising: (i) administering Compound 1 or a pharmaceutically acceptable salt thereof QD on days 1-21 of a first 21-day cycle; and (ii) administering bevacizumab Q3W on day 1 of the first 21-day cycle.

Embodiment No. 46: The use of embodiment 44 or embodiment 45, further comprising: (i) administering about 50-500 mg Compound 1 or a pharmaceutically acceptable salt thereof QD on days 1-21 of a first 21-day cycle; and (ii) administering about 5-20 mg/kg bevacizumab Q3W on day 1 of the first 21-day cycle. In one such embodiment, the dosing regimen includes 2 or more cycles as described herein.

Embodiment No. 47: The method of any one of embodiments 18-40 or use of any one of embodiments 41-46, wherein the alkylation of KRas$^{G12C}$ by Compound 1 or a pharmaceutically acceptable salt thereof is measured in the patient.

The following Examples are presented by way of illustration, not limitation.

EXAMPLES

Example 1: Preclinical Work

The Kirsten rat sarcoma viral oncogene homolog (KRAS) gene encodes a GTPase that plays a central role in mediating cell growth and survival signaling. Mutations in KRAS that result in amino acid substitutions at glycine 12 (G12), glycine 13 (G13), and glutamine 61 (Q61) are common in tumors and are associated with tumorigenesis and maintenance of aggressive tumor growth (Der et al. Proc Natl Acad Sci USA 1982; 79(11):3637-40; Parada et al. Nature 1982; 297(5866):474-8; Santos et al. Nature 1982; 298(5872):343-7; Taparowsky et al. Nature 1982; 300(5894):762-5; Capon et al. Nature 1983; 304(5926):507-13). The KRAS$^{G12C}$ mutation is prevalent in non-small cell lung cancer (NSCLC), colorectal cancer, and other tumor types (Prior et al. Cancer Res 2012; 72(10):2457-67; Vogelstein et al. Science 2013; 339(6127):1546-58). Compound 1 is an oral anti-cancer therapeutic agent that selectively targets KRAS$^{G12C}$, resulting in covalent and irreversible inhibition of KRAS$^{G12C}$. For the examples described herein, Compound 1 shall refer to the adipate salt of Compound 1 unless otherwise specified. Compound 1 does not target other mutations in KRAS, the wild-type form of KRAS, or other members of the RAS family. Treatment of KRAS$^{G12C}$-positive cells or tumors with Compound 1 results in decreased KRAS pathway signaling, suppression of cell/tumor cell growth, and induction of apoptosis. Constitutive RAS signaling in tumors alters the tumor microenvironment in multiple ways, including induction of multiple angiogenic and immunosuppressive cytokines, such as VEGF, IL-6, IL-8, GCSF, and GM-CSF. Combination strategies to target tumor-intrinsic KRAS-mediated growth and survival signaling in conjunction with agents that effectively target supporting tumor stromal pathways is therefore of strong therapeutic interest.

The in vivo anti-tumor efficacy of Compound 1 (50 mg/kg, PO, QD) alone or in combination with anti-VEGF in the NCI-H2122 (KRAS$^{G12C}$) NSCLC xenograft tumor model was assessed. Single agent Compound 1 treatment resulted in tumor stasis (98% tumor growth inhibition (TGI)), whereas single agent anti-VEGF treatment showed slow growth inhibition (70% TGI). These studies demonstrate that the combination of Compound 1 and anti-VEGF resulted in an initial improvement in early tumor response, and an increase in anti-tumor activity (102% TGI) relative to single agent Compound 1. All doses and combinations tested were tolerated based on minimal changes in body weight and overall animal condition.

Compound 1 (adipic acid salt) was a solution at a concentration of 11.5 mg/ml in 0.5% (w/v) methylcellulose. Anti-VEGFA B20.4.1.1 (Mu anti-VEGFA B20.4.1.1; hereafter referred to as anti-VEGF) was a solution in Histidine Buffer (20 nM Histidine Acetate, 240 nM Sucrose, 0.02% Tween 20™, pH5.5). The oral-dosed vehicle control was 0.5% (w/v) methylcellulose. The anti-gD isotype control (Hu anti-gD 5B6; hereafter referred to as Isotype Control) was a solution in saline.

Female nude mice that were 9-10 weeks old were obtained from Charles River Laboratory (Hollister, CA) weighing an average of 26.0 g. The mice were housed in standard rodent micro-isolator cages and were acclimated to study conditions at least 3 days before tumor cell implantation. Only animals that appeared to be healthy and that were free of obvious abnormalities were used for the study.

Human non-small lung carcinoma NCI-H2122 cells were obtained from the American Type Culture Collection (Rockville, MD) and harbor a G12C oncogenic mutation in K-RAS. Cells were cultured in vitro, harvested in log-phase growth, and resuspended in Hank's Balanced Salt Solution (HBSS) containing Matrigel (BD Biosciences; San Jose, CA) at a 1:1 ratio. The cells were then implanted subcutaneously in the right lateral thorax of 60 nude mice. Each mouse was injected with 10×10$^6$ cells in a volume of 100 μL. Tumors were monitored until they reached a mean tumor volume of 115-228 mm$^3$. Mice were distributed into four groups based on tumor volumes with n=10 mice per group. The mean tumor volume across all four groups was 146 mm$^3$ at the initiation of dosing.

Mice were given vehicle (100 μL 0.5% MC) or 50 mg/kg Compound 1 (expressed as free-base equivalents). The MC vehicle and Compound 1 were administered on a daily basis (QD) orally (PO) by gavage for 21 days in a volume of 100 μL. The isotope control and anti-VEGF antibodies were administered intravenously (IV) at 10 mg/kg for the first dose, and then dosed intraperitoneally (IP) at 5 mg/kg for subsequent doses on a twice weekly (BIW) schedule.

Tumor sizes and mouse body weights were recorded twice weekly over the course of the study. Mice were promptly euthanized when tumor volume exceeded 2000 mm$^3$ or if body weight loss was ≥20% of their starting weight.

TABLE 1

| Group | Treatment | Dose level (nng/kg)$^a$ | Route | Schedule | Days of Dosing | Dose Conc. (mg/mL)$^a$ | Dose Volume (mL/kg) |
| --- | --- | --- | --- | --- | --- | --- | --- |
| 1 | Vehicle | 0, 10/5 | PO | QD, BIW | 21 | 0, 2.3 | 4, 4 |
| 2 | Compound 1 | 50 | PO | PO | 21 | 11.5 | 4 |
| 3 | Anti-VEGF (B20.4.1.1) | 10/5 | PO | BIW | 21 | 2.3 | 4 |

TABLE 1-continued

| Group | Treatment | Dose level (nng/kg)[a] | Route | Schedule | Days of Dosing | Dose Conc. (mg/mL)[a] | Dose Volume (mL/kg) |
|---|---|---|---|---|---|---|---|
| 4 | Compound 1 + Anti-VEGF | 50 + 10/5 | PO | QD, BIW | 21 | 11.5, 2.3 | 4, 4 |

Conc. = concentration;
PO = orally;
QD = once daily.
Note:
Vehicle control were 0.5% (w/v) methylcellulose (100 µL); Isotype anti-gD Ab (10 mg/kg, IV first dose, followed by 5 mg/kg, IP, BIW)
[a]Dose levels and concentrations are expressed as free-base equivalents and were dosed once daily (QD) for 21 days.

All concentrations were calculated based on a mean body weight of 23 g for the nude mouse strain used in this study.

Tumor volumes were measured in two dimensions (length and width) using Ultra Cal-IV calipers (model 54-10-111; Fred V. Fowler Co.; Newton, MA) and analyzed using Excel, version 14.2.5 (Microsoft Corporation; Redmond WA). The tumor volume was calculated with the following formula:

$$\text{Tumor size} (\text{mm}^3) = (\text{longer measurement} \times \text{shorter measurement}^2) \times 0.5$$

Anti-tumor responses were noted with partial responses (PRs) being defined as a >50% decrease from the initial tumor volume and complete responses (CRs) being defined as a 100% decrease in tumor volume.

Animal body weights were measured using an Adventura Pro AV812 scale (Ohaus Corporation; Pine Brook, NJ). Percent weight change was calculated using the following formula:

$$\text{Body weight change (\%)} = [(\text{current body weight/initial body weight}) - 1] \times 100$$

A generalized additive mixed model (GAMM) was employed to analyze transformed tumor volumes over time as this approach addresses both repeated measurements from the same study subjects and modest dropouts before study end (Lin et al. Wiley Online Library; 1999; 61:381-400 and Liang Biometrical Journal. Wiley Online Library; 2005; 47:358-68). As tumors generally exhibit exponential growth, tumor volumes were subjected to natural log transformation before analysis.

Estimates of efficacy were obtained by calculating the percent difference between the daily average baseline-corrected AUC of the relevant group fits on the original (i.e., untransformed) scale over a common time period.

A generalized additive mixed model (GAMM) was also employed to analyze raw body weights (i.e., grams) over time. After data fitting, raw body weight data at each time point from all individual animals and all group fits were normalized and re-plotted separately in two distinct ways: 1) normalized to the starting weight and reported as a percentage to yield % body weight change and 2) normalized to the maximum weight to date and reported as a percentage to yield % body weight loss.

Figure 2:
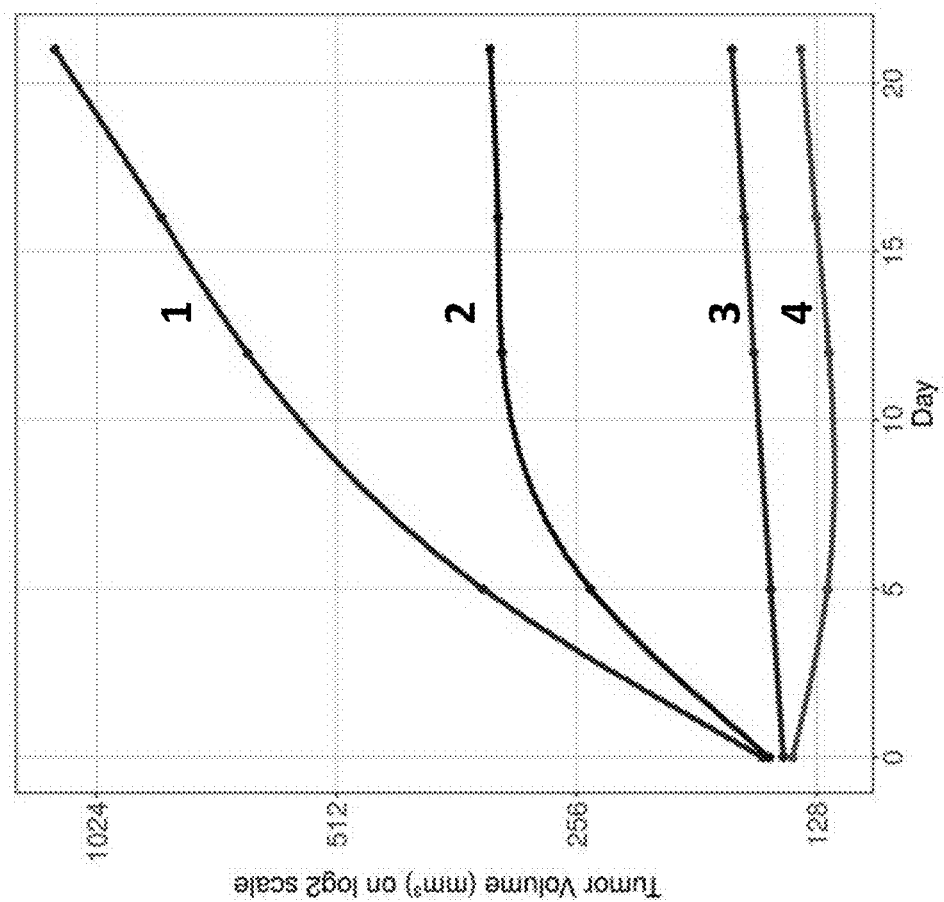
FIG. 2 illustrates tumor volumes of NCI-H2122 NSCLC tumor-bearing nude mice treated with Compound 1 as an adipate salt dosed alone or in combination with anti-VEGF antibody. Vehicles=0.5% (w/v) methylcellulose; Isotype anti-gD control antibody. Fitted group tumor volume after oral administration of Compound 1 dosed QD alone or in combination with anti-VEGF antibody dosed BIW for 21 days are depicted. Dose levels are expressed as free-base equivalents.

Anti-tumor efficacy was assessed in nude mice bearing human NCI-H2122 NSCLC xenografts following treatment with Compound 1 (50 mg/kg, PO, QD) alone compared to single agent anti-VEGF (10 mg/kg, IV, first dose, then 5 mg/kg, IP, BIW). The single agent treatments resulted in tumor growth inhibition (TGI). Compound 1 resulted in 98% TGI with 2/10 partial responses (PRs) and anti-VEGF resulted in 70% TGI with 0/10 PRs, relative to vehicle controls. In comparison, the combination of Compound 1 and anti-VEGF led to more consistent anti-tumor efficacy within the first week of treatment with only 2/10 mice showing increases in tumor volume, relative to 5/10 in the Compound 1 group and 9/10 in the anti-VEGF group. An improvement in anti-tumor efficacy relative to single agent Compound 1 was 102% TGI with 1/10 PRs (see FIG. 1 and FIG. 2).

TABLE 2

Summary of Anti-Tumor Activity of Compound 1 Dosed Alone or in Combination with Anti-VEGF in NCI-H2122 NSCLC Tumor Xenografts in Nude Mice

| Group (n = 10) | Treatment | Dose Levels (mg/kg) | TI | PR | CR | % TGI (estimated) | % TGI (lower CI) | % TGI (upper CI) |
|---|---|---|---|---|---|---|---|---|
| 1 | Vehicle | 0, 10/5 | 10/10 | 0 | 0 | 0 | 0 | 0 |
| 2 | Compound 1 | 50 | 10/10 | 2 | 0 | 98 | 90 | 103 |
| 3 | Anti-VEGF (B20) | 10/5 | 10/10 | 0 | 0 | 70 | 46 | 85 |
| 4 | Compound 1 + Anti-VEGF | 50 + 10/5 | 10/10 | 1 | 0 | 102 | 96 | 108 |

CI = confidence interval;
CR = complete response;
PR = partial response;
QD = once daily;
TI = tumor incidence.
Notes:
% TGI = percent of tumor growth inhibition based on AUC (see Data Analysis section for equation).
Vehicles = 0.5% (w/v) methylcellulose.

Combination anti-tumor efficacy studies were performed in the NCI-H2122 human NSCLC xenograft tumor model demonstrating that Compound 1 and anti-VEGF suppress tumor growth (98% TGI and 70% TGI, respectively) as single agents. Combination of Compound 1 with anti-VEGF led to anti-tumor response with 80% of mice (8/10) showing reductions in initial tumor size, relative to 50% (5/10) of mice in the Compound 1 group and 10% (1/10) in the anti-VEGF control arm. The anti-tumor activity for the Compound 1 and anti-VEGF combination showed improvement in anti-tumor efficacy (102% TGI) relative to Compound 1 alone (98% TGI). These data demonstrate that combination of Compound 1 with anti-VEGF is well-tolerated and has improvements in initial tumor response and overall anti-tumor activity in the NCI-H2122 human NSCLC human xenograft tumor model.

Example 2

KRAS is the most frequently mutated oncogene in up to 25% of cancers and is associated with resistance to select standard-of-care therapies and overall poor prognosis. Although selective inhibitors have been developed as anti-cancer therapy to target other nodes in the RAS/MAPK pathway, the KRAS oncoprotein was considered undruggable until the recent discovery of the switch II pocket (Ostrem, et al. Nature 2013; 503:548-51). With this finding, covalent small molecule inhibitors aimed at targeting KRAS, and specifically the $KRAS^{G12C}$ mutation, are being evaluated in early clinical development.

Other $KRAS^{G12C}$ inhibitors. AMG 510 (sotorasib) is a small molecule that irreversibly inhibits $KRAS^{G12C}$ by locking it in its inactive GDP-bound state. AMG-510 is currently being investigated in ongoing clinical studies. Patients in those studies received a median of 3 (range, 0 to 11) prior lines of anti-cancer therapies for metastatic disease before entering the study. Overall, treatment-related adverse events were reported in 56.6% of patients; 11.6% of patients experienced a treatment-related Grade 3 or 4 event, and 1.6% of patients experienced a treatment-related serious adverse event. Grade 3 events occurring in more than one patient included ALT increase, diarrhea, anemia, AST increase, and alkaline phosphatase increase. One patient experienced Grade 4 treatment-related ALT increase, and one patient discontinued AMG 510 due to Grade 3 treatment-related ALT and AST increase. While anti-tumor activity was reported, adverse events associated with AMG-510 exist. Patients had a confirmed objective response in 32.2% of patients with NSCLC and the median duration of response was 10.9 months (range, 1.1+ to 13.6) in patients. Median PFS was reported to be 6.3 months (range, 0.0+ to 14.9+) in patients with NSCLC (Hong et al. New Eng J Med 2020; 383:1207-17).

MRTX849 is a mutant-selective small molecule $KRAS^{G12C}$ inhibitor being evaluated in a clinical study of patients with advanced solid tumors with the $KRAS^{G12C}$ mutation. Data from a total of 17 patients (including 10 patients with NSCLC and 4 patients with CRC), of which 12 patients had undergone at least one on-treatment tumor assessment (including 6 patients with NSCLC and 4 patients with CRC), were reported recently. Most patients had received 3 or more prior anti-cancer regimens before study entry (12 of 17 patients, 71%). The following treatment-related adverse events were reported in >10% of patients: diarrhea, nausea, AST increased, vomiting, fatigue, ALT increased, creatinine increased, abdominal distension, abdominal pain, ALP increased, anemia, decreased appetite, dehydration, dry mouth, dysgeusia, dyspnea, QT prolonged, hypomagnesemia, and rash. Grade 3 events included fatigue, decreased appetite, and dyspnea (1 patient each). Anti-tumor activity with PR was achieved in 3 of 6 patients with NSCLC and 1 of 4 patients with CRC across all dose levels evaluated (Janne et al. AACR-NCI-EORTC International Conference on Molecular Targets and Cancer Therapeutics October 2019).

Compound 1. The specificity of Compound 1 for $KRAS^{G12C}$, together with its mechanism of action, leads to potent and irreversible inhibition of $KRAS^{G12C}$, and is expected to enable a broad therapeutic index, maximizing anti-tumor activity while minimizing treatment-related toxicities. Specific therapies aimed at $KRAS^{G12C}$-positive cancer may provide more tolerable and effective treatment options for patients with advanced stage cancers that harbor $KRAS^{G12C}$.

In vitro and in vivo pharmacology studies demonstrate that Compound 1 is a highly potent and selective covalent inhibitor of $KRAS^{G12C}$, exhibiting over 20,000-fold selectivity in growth inhibition for $KRAS^{G12C}$-positive over $KRAS^{G12C}$-negative cancer cell lines. Mechanism of action studies with Compound 1 demonstrate that downstream MAPK pathway components such as phosphorylated (p)ERK and pS6, in addition to KRAS target genes such as DUSP6 and SPRY4, are inhibited and apoptosis induction is observed in $KRAS^{G12C}$-positive cancer cell lines. In addition, Compound 1 has potent single-agent activity and inhibits tumor growth in a number of nonclinical xenograft models of $KRAS^{G12C}$-positive lung tumors. These in vitro and in vivo pharmacology studies support the use of Compound 1 for the treatment of patients with locally advanced or metastatic $KRAS^{G12C}$-positive solid tumors.

The results of nonclinical toxicology studies completed to date provide a robust characterization of the toxicity profile of Compound 1 and support the administration of Compound 1 in patients with cancer. Comprehensive nonclinical toxicity studies were completed to evaluate the potential single and repeat dose oral toxicity, genetic toxicity, phototoxicity, and safety pharmacology of Compound 1. Because the $KRAS^{G12C}$ mutation is not present in healthy animals, there are no pharmacologically relevant nonclinical species for $KRAS^{G12C}$ inhibition.

Bevacizumab is a recombinant humanized IgG1 monoclonal antibody that is specifically directed against vascular endothelial growth factor (VEGF) that recognizes all isoforms of VEGF. It contains human framework regions and murine complementarity-determining regions. It may exert a direct anti-angiogenic effect by binding to and clearing VEGF from the tumor environment. Additional anti-tumor activity may be derived from its effects on tumor vasculature, interstitial pressure, and blood vessel permeability, providing for enhanced chemotherapy delivery to tumor cells (Jain, Nat Med 2001; 7:987-9).

Bevacizumab is approved for the treatment of a number of different solid tumor types, including metastatic colorectal cancer, advanced NSCLC, unresectable or metastatic hepatocellular carcinoma, metastatic breast cancer, advanced renal cell carcinoma, ovarian cancer, and treatment of recurrent glioblastoma.

Early Phase I clinical data from the ongoing studies of AMG 510 and MRTX849 as single agents have shown that $KRAS^{G12C}$ inhibitors are tolerable and have promising anti-tumor activity in patients with metastatic NSCLC and CRC (Janne et al. 2019; Hong et at. New Eng J Med 2020; 383:1207-17). However, there still remains a great unmet need to improve upon the anti-tumor activity and durability reported in NSCLC and CRC with this class of inhibitors as a single agent while importantly retaining their tolerable safety profile.

Rationale for Combination Therapy with Bevacizumab. Increased expression and the poor prognostic role of VEGF have been reported in most solid tumors (Zhan et al. J Thorac Oncol 2009; 4:1094-103; Gentzler et al. Curr Treat Options Oncol 2013; 14:595-609). Elevated VEGF mRNA levels were detected in tumor cell lines expressing mutant KRAS, whereas genetic disruption of the mutant KRAS allele in human colon carcinoma cells resulted in decreased VEGF secretion (Rak et al. N Eng J Med 2016; 375:1823-33).

The VEGF pathway also plays a crucial role in exerting and maintaining an immunosuppressive tumor microenvironment through several mechanisms. For instance, VEGF-A has been shown to induce FasL expression on endothelial cells, which have the ability to kill effector CD8+ T cells, but not T-reg cells. Administration of anti-VEGF-A attenuated tumor endothelial FasL expression and produced a significant increase in the influx of tumor-rejecting CD8+ over FoxP3+ T cells, which was FasL-dependent, and led to CD8-dependent tumor growth suppression (Motz et al. 2014). In contrast, bevacizumab can restore and/or maintain the antigen presentation capacity of dendritic cells, leading to enhanced T-cell infiltration in tumors (Oelkrug and Ramage Clin Exp Immunol 2014; 178:1-8; Wallin et al. Nat Commun 2016; 7:12624). In addition to increased trafficking of T cells into tumors (Manning et al. Clin Cancer Res 2007; 13:3951-9), several publications have shown that anti-VEGF therapies can also reduce frequency of myeloid-derived suppressor cells, decrease production of suppressive cytokines, and lower expression of inhibitory checkpoints on CD8+ T cells in tumors (Roland et al. PLOS One 2009; 4:e7669; Voron et al. J Exp Med 2015; 212:139-48). Thus, the immunomodulatory effect of bevacizumab is expected to increase CD8-positive T-cell recruitment and relieve intratumoral immunosuppression.

Given the growing evidence suggesting that both $KRAS^{G12C}$ inhibition and VEGF-inhibition have immunomodulatory effects that can relieve intratumoral immune suppression and increase T-cell infiltration, there is scientific rationale to combine $KRAS^{G12C}$ inhibition with VEGF blockade.

In in vivo mouse studies, combination of Compound 1 with anti-VEGF monoclonal antibody treatment resulted in an increase in initial tumor response relative to Compound 1 alone and improvement in overall anti-tumor efficacy.

Compound 1 will be investigated in combination bevacizumab in patients with advanced or metastatic $KRAS^{G12C}$-positive solid tumors. The dose of bevacizumab in combination with Compound 1 will be 15 mg/kg IV on Day 1 of each 21-day cycle. Potential overlapping toxicities include gastrointestinal toxicities, and are expected to be monitorable and manageable with supportive care and potentially dose modifications.

This study will assess the activity of Compound 1 in combination with bevacizumab on the basis of the following endpoints: Objective response rate (ORR); Duration of response (DOR); and Progression-free survival (PFS).

Biomarkers. This study will identify and/or evaluate biomarkers that are predictive of response to Compound 1 as a single agent or in combination with bevacizumab (i.e., predictive biomarkers), early surrogates of activity, associated with progression to a more severe disease state (i.e., prognostic biomarkers), associated with acquired resistance to $KRAS^{G12C}$ inhibitors (e.g., Compound 1), associated with susceptibility to developing adverse events or can lead to improved adverse event monitoring or investigation (i.e., safety biomarkers), can provide evidence of Compound 1 activity in combination with bevacizumab (i.e., pharmacodynamic [PD] biomarkers), or can increase the knowledge and understanding of disease biology and drug safety. Corresponding biomarker endpoints include the relationship between exploratory biomarkers in blood, plasma, and tumor tissue and safety, PK, activity, or other biomarker endpoints.

Patients are screened for period of up to 28 days, followed by a treatment period, and a safety follow-up period during which patients will be followed for safety outcomes for a treatment-specific period after their final dose of study drug or until they receive another anti-cancer therapy, whichever occurs first.

In the absence of unacceptable toxicities and unequivocal disease progression as determined by the investigator, patients may continue treatment with Compound 1.

All patients will be closely monitored for adverse events throughout the study and for a treatment-specific period after the final dose of study treatment or until initiation of another anti-cancer therapy, whichever occurs first. Adverse events will be graded according to the NCI CTCAE v5.0.

The starting dose of Compound 1 will be 50 mg PO QD. Single-patient dose-escalation cohorts will be treated at escalating dose levels of Compound 1.

Patients include those with locally advanced, recurrent, or metastatic incurable $KRas^{G12C}$-positive tumors (e.g. NSCLC, CRC, hepatocellular carcinoma, breast cancer, renal cell carcinoma, endometrial cancer, ovarian cancer, or pancreatic cancer) who have disease progression or intolerance to at least one prior systemic therapy that may include single-agent or combination therapy. Patient having NSCLC, CRC, or pancreatic cancer will be screened for $KRas^{G12C}$-positivity.

$KRas^{G12C}$ Mutation Status from Tissue and Circulating Tumor DNA Assessments. Approximately 12% of NSCLC, 4% of CRC, 2% of pancreatic cancers, and many other solid tumors (prevalence≤4% in each) harbor the $KRas^{G12C}$ mutation. Compound 1 is a potent and highly selective inhibitor that targets $KRas^{G12C}$, but not other mutations in KRAS, the wild-type form of KRAS, or other members of the RAS family. Therefore, only patients with tumors harboring the $KRas^{G12C}$ mutation are eligible for administration of combination therapies described herein. KRAS mutation status may be determined using the FoundationOne® CDx (F1CDx) assay, a U.S. Food and Drug Administration (FDA)-approved broad companion diagnostic (CDx) assay, FoundationOne® Liquid CDx (F1L CDx) assay, as well as other FDA approved (FDA 2020) or well-validated laboratory developed tests performed in a Clinical Laboratory Improvement Amendments (CLIA)-validated or equivalently certified laboratory. Previous studies indicate that occurrence of the $KRas^{G12C}$ mutation is an early event (Jamal-Hanjani et al. N Engl J Med 2017; 376:2109-21), suggesting that analysis of archival tissue is a sufficient surrogate for selection of patients with $KRas^{G12C}$-positive tumors for Compound 1 treatment.

Pharmacodynamic Pathway Modulation. Compound 1 is a $KRas^{G12C}$ inhibitor that suppresses downstream MAPK signaling by alkylation of $KRas^{G12C}$, thereby locking it in its inactive GDP-bound state. In nonclinical models, the level of $KRas^{G12C}$ alkylation by Compound 1 and the extent of MAPK pathway suppression correlate with response to Compound 1. Pre-treatment and on-treatment tumor tissue collection will enable an assessment of the correlation of MAPK pathway suppression and anti-tumor activity with Compound 1 treatment. The extent of MAPK pathway suppression can be assessed using RNA analysis of MAPK target genes (e.g., DUSP6, SPRY4) or immunohistochemistry (IHC) analysis of phosphorylated downstream markers (e.g., pERK, pS6). In addition, on-treatment tumor tissue biopsies may enable direct assessment of the level of $KRas^{G12C}$ alkylation by Compound 1. The assessment of these PD biomarkers may inform future dose selection.

Sequencing of Genes Related to Resistance to Compound 1. DNA sequencing techniques, such as targeted next-generation sequencing (NGS) and whole exome sequencing, may offer a unique opportunity to identify biomarkers of response and/or resistance to Compound 1. Sequencing of cancer-related genes may result in the identification of de novo and acquired mechanisms of resistance to Compound 1.

Protein, RNA, and DNA Analysis. Evaluation of the signaling activities (e.g., MAPK, PI3K/AKT) in tumor cells in the tumor microenvironment could provide valuable insights in the sensitivity or resistance to Compound 1 treatment as a single agent or in combination therapy. VEGF expression assessed by IHC may be performed for the analysis of anti-tumor activity in subgroups based on VEGF expression.

In addition to mutational activation of proteins, expression levels of RNA or alterations in DNA may also modulate the activity of signaling pathways. RNA profiling of tumors will allow intrinsic subtyping of patients enrolled in the study. Analysis of the potential association between subtypes and patient outcome may identify subpopulations of patients who are most likely to respond to Compound 1.

Plasma Sample for Somatic Tumor Mutation Analysis and Other Biomarkers. There is increasing evidence that cell-free DNA obtained from blood specimens of patients with cancer contains ctDNA, which is representative of the DNA and mutational status of cells in the tumor (Diehl et al. 2008; Maheswaran et al. 2008). Assays have been validated to detect cancer-related mutations (e.g., KRAS) from plasma. Results of these assays may be correlated with the mutational status determined from analysis of tumor specimens. The use of ctDNA to monitor response to treatment is an area of great interest, and could allow for an early, non-invasive, and quantifiable method for use in the clinical setting to identify candidates for specific therapies and monitoring of mutation status of the cancer over time (Wan et al. Nat Rev Cancer 2017; 17:223-38). Analysis of ctDNA collected at various times during study treatment and after a patient progresses on Compound 1 may help to identify mechanisms of response and acquired resistance to study treatment.

Blood Sample for Next-Generation Sequencing. Next-generation sequencing (NGS) technologies can generate a large quantity of sequencing data. Tumor DNA can contain both reported and unreported chromosomal alterations because of the tumorigenesis process. To help control for sequencing calls in previously unreported genomic alterations, a predose blood sample will be taken to determine whether the alteration is somatic.

Inclusion Criteria. Patients must meet the following criteria for study entry:
Age≥18 years;
Evaluable or measurable disease per RECIST v1.1;
Eastern Cooperative Oncology Group (ECOG) performance status of 0 or 1;
Life expectancy of ≥12 weeks;
Adequate hematologic and organ function within 14 days prior to initiation of study treatment, defined by the following:
  Absolute neutrophil count≥1200/µL;
  Hemoglobin≥9 g/dL;
  Platelet count≥100,000/µL;
  Total bilirubin≤1.5×ULN;
  Serum albumin≥2.5 g/dL;
  AST and ALT≤2.5×ULN with the following exception:
    Patients with documented liver metastases may have AST and/or ALT≤5.0×ULN.
  Serum creatinine≤1.5×ULN or creatinine clearance≥50 mL/min on the basis of the Cockcroft-Gault glomerular filtration rate estimation:

$$\frac{(140 - \text{age}) \times (\text{weight in kg}) \times (0.85 \text{ if female})}{72 \times (\text{serum creatinine in mg/dL})}$$

For women of childbearing potential: Agreement to remain abstinent (refrain from heterosexual intercourse) or use contraception, and agreement to refrain from donating eggs;
For men who are not surgically sterile: Agreement to remain abstinent (refrain from heterosexual intercourse) or use contraception, and agreement to refrain from donating sperm;
Confirmation of biomarker eligibility: Valid results from either central testing of blood or local testing of blood or tumor tissue documenting the presence of the $KRas^{G12C}$ mutation (e.g. validated polymerase chain reaction (PCR)-based or NGS assay performed at a CLIA or equivalently certified laboratory).

Additional Inclusion Criteria

Histologically documented, locally advanced, recurrent, or metastatic incurable solid tumor
  Disease progression after at least one available standard therapy; or for whom standard therapy has proven to be ineffective or intolerable, or is considered inappropriate; or for whom a clinical trial of an investigational agent is a recognized standard of care
  If a patient that has progressed after at least one available standard therapy has additional approved standard treatment options available, the study doctor must discuss the risks and benefits of those treatments before informed consent to participate in this study is obtained. This discussion must be documented in patient records.
Patients with NSCLC and adenocarcinoma of the colon or rectum must not have a known concomitant second oncogenic driver (e.g., for NSCLC: sensitizing EGFR mutations, ALK rearrangement, ROS1 rearrangement, BRAF V600E mutation, NTRK fusions, RET fusions; or for adenocarcinoma of the colon or rectum: BRAF V600E mutation, ERBB2 amplification) as determined by the FMI NGS assay or by a Sponsor-approved validated PCR-based or NGS assay performed at a local CLIA-certified or equivalently-certified laboratory.

General Exclusion Criteria. Patients who meet any of the following criteria will be excluded:
Inability or unwillingness to swallow pills;
Inability to comply with study and follow-up procedures;

Malabsorption syndrome or other condition that interferes with enteral absorption;

Known and untreated, or active central nervous system (CNS) metastases;

Patients with a history of treated CNS metastases provided they meet all of the following criteria:
Measurable or evaluable disease outside the CNS;
No history of intracranial hemorrhage or spinal cord hemorrhage;
No ongoing requirement for corticosteroids as therapy for CNS metastases, with corticosteroids discontinued for ≥2 weeks prior to administration of an agent described herein and no ongoing symptoms attributed to CNS metastases;
No stereotactic radiation within 7 days or whole-brain radiation within 14 days prior to Day 1 of Cycle 1;
No evidence of interim progression between the completion of CNS-directed therapy and the screening radiographic study;

Leptomeningeal disease or carcinomatous meningitis;

Uncontrolled pleural effusion, pericardial effusion, or ascites requiring recurrent drainage procedures biweekly or more frequently;
Indwelling pleural or abdominal catheters may be allowed, provided the patient has adequately recovered from the procedure, is hemodynamically stable and symptomatically improved;

Any active infection that could impact patient safety, or serious infection requiring IV antibiotics within 7 days prior to Day 1 of Cycle 1;

Clinically significant history of liver disease, including viral or other hepatitis, current alcohol abuse, or cirrhosis;

Known HIV infection;

Uncontrolled hypercalcemia (>1.5 mmol/L ionized calcium or calcium>12 mg/dL or corrected serum calcium≥ULN) or symptomatic hypercalcemia requiring continued use of bisphosphonate therapy or denosumab;

Significant traumatic injury or major surgical procedure within 4 weeks prior to Day 1 of Cycle 1;

Patients with chronic diarrhea, short bowel syndrome or significant upper gastrointestinal surgery including gastric resection, a history of inflammatory bowel disease (e.g., Crohn's disease or ulcerative colitis) or any active bowel inflammation (including diverticulitis);

Treatment with chemotherapy, immunotherapy, or biologic therapy as anti-cancer therapy within 3 weeks prior to administration of an agent described herein, or endocrine therapy within 2 weeks prior administration of an agent described herein, except for the following:
Hormonal therapy with gonadotropin-releasing hormone (GnRH) agonists or antagonists for endocrine sensitive cancers (e.g., prostate, endometrial, hormone receptor-positive breast cancer);
Kinase inhibitors, approved by regulatory authorities, may be used up to 2 weeks prior to initiation of study treatment;

Treatment with an investigational agent within 3 weeks or five half-lives prior to administration of an agent described herein, whichever is shorter.

Radiation therapy (other than palliative radiation to bony metastases and radiation to CNS metastases) as cancer therapy within 4 weeks prior to administration of an agent described herein;

Palliative radiation to bony metastases within 2 weeks prior to administration of Compound 1;

Adverse events from prior anti-cancer therapy that have not resolved;

History of other malignancy within 5 years prior to screening;

History of or active clinically significant cardiovascular dysfunction, including:
History of stroke or transient ischemic attack within 6 months prior to administration of an agent described herein;
History of myocardial infarction within 6 months prior to administration of an agent described herein;
New York Heart Association Class III or IV cardiac disease or congestive heart failure requiring medication
Uncontrolled arrhythmias, history of or active ventricular arrhythmia requiring medication;
Coronary heart disease that is symptomatic or unstable angina;
Congenital long QT syndrome or QT interval corrected through use of Fridericia's formula (QTcF)>470 ms;
Current treatment with medications known to prolong the QT interval;

Pregnant or breastfeeding, or intending to become pregnant during the study or within 6 months after the final dose of Compound 1;

Poorly controlled hypertension (e.g., systolic>150 mmHg or diastolic>100 mmHg)

History or evidence of inherited bleeding diathesis or coagulopathy with the risk of bleeding Current or recent (<10 days prior to initiation of study treatment) use of aspirin (>325 mg/day), or clopidogrel (>75 mg/day)

History of thrombotic disorders within the last 6 months prior to initiation of study treatment ≥2+ proteinuria on dipstick urinalysis during screening or at planned Cycle 1 Day 1 assessment should undergo a 24-hour urine collection and must demonstrate ≤1 g of protein in 24 hours prior to initiation of study treatment.

Serious, non-healing wound, active ulcer, or untreated bone fracture

History of abdominal fistula, gastrointestinal perforation or intra-abdominal abscess within 6 months of initiation of study treatment Pulmonary hemorrhage/hemoptysis (>½ teaspoon red blood) within one month prior to initiation of study treatment Clear tumor infiltration into the thoracic great vessels seen on imaging Clear cavitation of pulmonary lesions seen on imaging Study Treatment Formulation, Packaging, and Handling Compound 1. Compound 1 will be supplied as an active pharmaceutical ingredient (API) powder-in-capsule (PIC) formulation in three strengths: 5 mg, 25 mg, and 100 mg (free base equivalent). Additionally, a film-coated tablet formulation in a dose strength of 100 mg (free base equivalent) will also be supplied for clinical use. Compound 1 drug products should be stored at or below 86° F. (30° C.) and protected from moisture.

For Compound 1 doses to be administered at home, a sufficient number of capsules or tablets should be dispensed to the patient to last until the next visit or through one cycle. Patients will self-administer Compound 1 as provided herein, except when patients visit a clinic. Patients should take Compound 1 at approximately the same time each day unless otherwise instructed. Patients will be instructed as to the number and strength of capsules or tablets to take, according to their assigned dose level and schedule.

Unless otherwise instructed, Compound 1 should be taken on an empty stomach, i.e., food should be avoided at least 2 hours before as well as 1 hour after the dose is administered. There are no restrictions on water intake. Importantly, Compound 1 capsules or tablets will be swallowed whole (not chewed) with a minimum of 240 mL (8 fluid ounces) of water. If a patient misses any dose of Compound 1 or vomits up a capsule or tablet, the patient should be instructed to skip that dose and resume dosing with the next scheduled dose. Missed doses will not be made up.

Bevacizumab. Bevacizumab will be supplied as an IV formulation in 400 mg/16 ml vials. Bevacizumab will be administered by IV infusion at a fixed dose of 15 mg/kg IV on Day 1 of each 21-day cycle, following administration of Compound 1. Administration of bevacizumab will be performed in a monitored setting where there is immediate access to trained personnel and adequate equipment and medicine to manage potentially serious reactions. Bevacizumab will be diluted in 0.9% sodium chloride injection, USP, to a total volume of 100 mL. The initial dose will be delivered over 90±15 minutes. If the first infusion is tolerated without any infusion-associated adverse events (i.e., fever and/or chills), the second infusion may be delivered over 60±10 minutes. If the 60-minute infusion is well tolerated, all subsequent infusions may be delivered over 30±10 minutes. Bevacizumab infusions may be slowed or interrupted for patients experiencing infusion-associated symptoms. If infusion-related symptoms occur, patients should be treated according to best medical practice.

In the event bevacizumab administration is held due to an adverse event in a given cycle, the next dosing cycle should not begin until administration of bevacizumab can be resumed. As such, the current cycle may be extended past 21 days, and the patient may continue to receive Compound 1. Day 1 of the next cycle should correspond to the timepoint at which administration of bevacizumab is resumed. No dose modification for bevacizumab is allowed.

Concomitant Therapy. Concomitant therapy consists of any medication (e.g. prescription drugs, over-the-counter drugs, vaccines, herbal or homeopathic remedies, nutritional supplements) used by a patient in addition to an agent described herein from 7 days prior to the first administration of at least one agent described herein to the last administration of at least one agent described herein.

Permitted Therapy. Patients may take (a) anti-seizure medications or warfarin; (b) oral contraceptives or other allowed maintenance therapy as specified in the eligibility criteria; (c) anti-emetics and anti-diarrheal medications should not be administered prophylactically before initial treatment with study drug; (d) pain medications; (e) bisphosphonate and denosumab therapy for bone metastases or osteopenia or osteoporosis; or multivitamins, calcium, and vitamins C, D, and E supplements are allowed.

Precautionary Therapy. Medications Given with Precaution due to Effects Related to CYP Enzymes and Compound 1 include, for example, (1) Strong/moderate CYP3A4 inhibitors, including, but not limited to, the following: atazanavir, ritonavir, indinavir, nelfinavir, saquinavir, clarithromycin, telithromycin, erythromycin, troleandomycin, fluconazole, itraconazole, ketoconazole, voriconazole, posaconazole, aprepitant, conivaptan, fluvoxamine, diltiazem, nefazodone, mibefradil, verapamil, and grapefruit juice or grapefruit supplements; (2) Strong/moderate CYP3A4 inducers, including, but not limited to, the following: rifampin, carbamazepine, phenytoin, oxcarbazepine, phenobarbital, efavirenz, nevirapine, etravirine, modafinil, hyperforin (St. John's Wort), and cyproterone. The use of full-dose oral or parenteral anticoagulants for therapeutic purpose as long as the INR and/or aPTT is within therapeutic limits (according to institution standards) within 14 days prior to administration of any agent described herein and the patient has been on a stable dose of anticoagulants for ≥1 week prior to initiation of study treatment. The lists of medications are not intended to be comprehensive.

Prohibited Therapy. Use of the following concomitant therapies is prohibited during and for at least 7 days prior to the first administration of an agent described herein:

Investigational therapy within 3 weeks or five half-lives prior to the first administration of an agent described herein, whichever is shorter;
  Concomitant therapy intended for the treatment of cancer whether approved by the FDA or experimental, including chemotherapy, radiotherapy, immunotherapy, biologic therapy, herbal therapy, or hormonal therapy except for the following:
    Hormonal therapy with gonadotropin-releasing hormone (GnRH) agonists or antagonists for endocrine sensitive cancers (e.g. prostate, endometrial, hormone receptor-positive breast cancer);
  Hormone replacement therapy or oral contraception.
  Radiotherapy for unequivocal progressive disease with the exception of new brain metastases in the setting of systemic response: patients who have demonstrated control of their systemic disease (defined as having received clinical benefit [i.e., a PR, CR, or SD for ≥3 months]), but who have developed brain metastases that are treatable with radiation, will be allowed to continue to receive therapy with Compound 1 during the study until they either experience systemic progression of their disease and/or further progression in the brain (based on investigator assessments);
  Quinidine or other anti-arrhythmic agents;
  Initiation or increased dose of hematopoietic colony-stimulating factors (CSFs; e.g., granulocyte CSF; filgrastim, granulocyte/macrophage CSF; sargramostim, pegfilgrastim, erythropoietin, darbepoetin, and thrombopoietin) from 7 days before Cycle 1, Day 1

Risks Associated with Compound 1. Administration of Compound 1 has been associated diarrhea, nausea, vomiting, oral mucosal irritation, minimal to mild transaminase elevation, and phototoxicity.

Risks Associated with Bevacizumab. Bevacizumab has been associated with risks such as the following: gastrointestinal perforations, surgery and wound healing complications, hemorrhage (severe or fatal hemorrhage including hemoptysis, gastrointestinal bleeding, hematemesis, CNS hemorrhage, pulmonary hemorrhage, epistaxis, and vaginal bleeding), non-gastrointestinal fistula formation, arterial thromboembolic events (including cerebral infarction, transient ischemic attacks, myocardial infarction, angina), and hypertension.

Potential overlapping toxicities associated with combination use of bevacizumab and Compound 1 are gastrointestinal toxicities.

Treatment Interruption. If Compound 1 is held for >21 days from the previous study treatment due to toxicity, the study treatment should not be re-initiated. Compound 1 may be suspended for up to 21 days for unanticipated intercurrent medical events that are not associated with study treatment toxicity or disease progression.

Adverse Events. An adverse event as defined herein refers to any untoward medical occurrence in a clinical investigation subject administered an agent described herein in the combination therapies described herein, regardless of causal attribution. The terms "severe" and "serious" are not synonymous. Severity refers to the intensity of an adverse event (e.g., rated as mild, moderate, or severe, or according to NCI CTCAE); the event itself may be of relatively minor medical significance (such as severe headache without any further findings).

Adverse events to be monitored include nausea, vomiting, diarrhea, stomatitis, mucositis, hepatitis or elevation in ALT or AST, elevated bilirubin or clinical jaundice, systemic lupus erythematosus, nephritis, Events suggestive of hypersensitivity, infusion-mediated reactions, CRS, influenza-like illness, and systemic inflammatory response syndrome, atrial fibrillation, myocarditis, pericarditis, Vasculitis, Myositis, uveitis, retinitis, optic neuritis, autoimmune hemolytic anemia, Stevens-Johnson syndrome, dermatitis bullous, and toxic epidermal necrolysis.

Throughout this specification and the claims, the words "comprise," "comprises," and "comprising" are used in a non-exclusive sense, except where the context requires otherwise. It is understood that embodiments described herein include "consisting of" and/or "consisting essentially of" embodiments.

Where a range of values is provided, it is understood that each intervening value, to the tenth of the unit of the lower limit, unless the context clearly dictates otherwise, between the upper and lower limit of the range and any other stated or intervening value in that stated range, is encompassed herein. The upper and lower limits of these small ranges which can independently be included in the smaller rangers is also encompassed herein, subject to any specifically excluded limit in the stated range. Where the stated range includes one or both of the limits, ranges excluding either or both of those included limits are also included herein.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A method of treating colorectal cancer (CRC) mediated by a KRas$^{G12C}$ mutation in a patient having CRC, the method comprising administering:

(a)

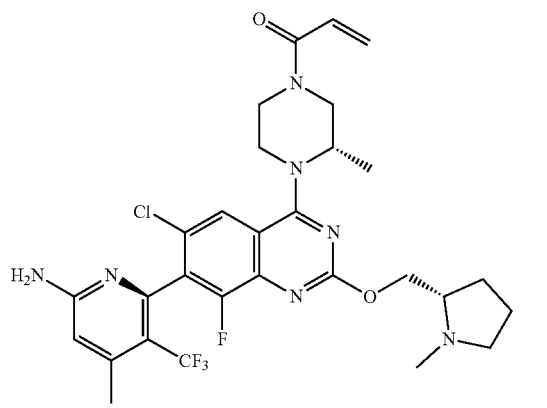

Compound 1 or an adipate salt thereof QD at an effective amount of about 50 mg-500 mg QD on days 1-21 of a first 21-day cycle; and (b) an effective amount of bevacizumab Q3W on day 1 of the first 21-day cycle.

2. The method of claim 1, wherein Compound 1 or an adipate salt thereof is administered orally as a tablet or capsule.

3. The method of claim 1, wherein Compound 1 or an adipate salt thereof is administered at an amount of about 50 mg, 100 mg, 200 mg, 300 mg, or 400 mg.

4. The method of claim 1, wherein Compound 1 or an adipate salt thereof is administered at an amount of about 200 mg.

5. The method of claim 1, wherein Compound 1 or an adipate salt thereof is administered at an amount of about 400 mg.

6. The method of claim 1, wherein bevacizumab is administered Q3W at an amount of about 5-20 mg/kg.

7. The method of claim 1, wherein bevacizumab is administered Q3W at an amount of about 10-20 mg/kg.

8. The method of claim 1, wherein bevacizumab is administered Q3W to the patient intravenously at a dose of about 15 mg/kg.

9. The method of claim 1, wherein bevacizumab is administered after administration of Compound 1 or a pharmaceutically acceptable salt thereof.

10. The method of claim 1, wherein:
(a) Compound 1 or an adipate salt thereof is administered at an amount of about 200 mg or 400 mg QD; and
(b) bevacizumab is administered Q3W at an amount of 15 mg/kg.

11. The method of claim 1, wherein the patient has previously progressed disease having had bevacizumab as a component of a first-line therapy.

12. The method of claim 1, wherein the CRC is metastatic CRC (mCRC).

13. The method of claim 1, wherein the administration of Compound 1 or an adipate salt thereof and bevacizumab is a first-line treatment for CRC comprising a KRas$^{G12C}$ mutation.

14. The method of claim 1, wherein the administration of Compound 1 or an adipate salt thereof and bevacizumab is a second-line treatment for CRC comprising a KRas$^{G12C}$ mutation.

15. The method of claim 1, wherein the administration further comprises administration of fluoropyrimidine-irinotecan based chemotherapy.

16. The method of claim 1, wherein the administration further comprises administration of fluoropyrimidine-oxaliplatin based chemotherapy.

17. The method of claim 1, wherein the patient has not received treatment with chemotherapy, immunotherapy, or biologic therapy as anti-cancer therapy within 3 weeks prior to administration of Compound 1 or an adipate salt thereof and bevacizumab.

18. The method of claim 1, wherein the patient has not received treatment with endocrine therapy within 2 weeks prior to administration of Compound 1 or an adipate salt thereof and bevacizumab.

19. The method of claim 1, alkylation of KRas$^{G12C}$ by Compound 1 or the adipate salt thereof is measured in the patient.

* * * * *